(12) United States Patent
Figeys et al.

(10) Patent No.: US 6,576,896 B2
(45) Date of Patent: Jun. 10, 2003

(54) ELECTROOSMOTIC FLUIDIC DEVICE AND RELATED METHODS

(75) Inventors: Daniel Figeys, Seattle, WA (US); Ruedi Aebersold, Mercer Island, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/053,485

(22) Filed: Jan. 23, 2002

(65) Prior Publication Data

US 2003/0047680 A1 Mar. 13, 2003

Related U.S. Application Data

(63) Continuation of application No. 09/209,880, filed on Dec. 11, 1998, now abandoned.
(60) Provisional application No. 60/069,398, filed on Dec. 12, 1997.

(51) Int. Cl.[7] .................................................. H01J 49/00
(52) U.S. Cl. ..................................................... 250/288
(58) Field of Search .......................... 250/288; 204/600, 204/601, 609, 450, 451, 453, 454

(56) References Cited

U.S. PATENT DOCUMENTS

| | | |
|---|---|---|
| 5,505,832 A | 4/1996 | Laukien et al. |
| 5,993,633 A | 11/1999 | Smith et al. |
| 6,043,487 A | 3/2000 | Waki |
| 6,103,199 A | 8/2000 | Bjornson et al. |
| 6,149,815 A | 11/2000 | Sauter |

OTHER PUBLICATIONS

Effenhauser, C.S., et al., "Glass Chips for High–Speed Capillary Electrophoresis Separations with Submicrometer Plate Heights", *Analytical Chemistry*, vol. 65, No. 19, Oct. 1, 1993, pp. 2637–2642.

Harrison, D.J., et al., "Micromachining a Miniaturized Capillary Electrophoresis–Based Chemical Analysis System on a Chip," *Science*, vol. 261, Aug. 13, 1993, pp. 895–897.

Harrison, D.J., et al., "Micromachining Chemical and Biochemical Analysis and Reaction Systems on Glass Substrates," *Sensors and Actuators B–Chemical*, vol. 33, 1996, pp. 105–109.

Jacobson, S.C., et al., "High–Speed Separations on a Microchip," *Analytical Chemistry*, vol. 66, No. 7, Apr. 1, 1994, pp. 1114–1118.

Jacobson, S.C., et al., "Microchip Capillary Electrophoresis with an Integrated Postcolumn Reactor," *Analytical Chemistry*, vol. 66, No. 20, Oct. 15, 1994, pp. 3472–3476.

Kutter, J.P., et al., "Integrated Microchip Device with Electrokinetically Controlled Solvent Mixing for Isocratic and Gradient Elution in Micellar Electrokinetic Chromatography," *Analytical Chemistry*, vol. 69, No. 24, Dec. 15, 1997, pp. 5165–5171.

Ramsey, J.M., et al., "Microfabricated Chemical Measurement Systems," *Nature Medicine*, vol. 1, No. 10, Oct. 1995, pp. 1093–1096.

Ramsey, R.S., et al., "Generating Electrospray from Microchip Devices Using Electroosmotic Pumping," *Analytical Chemistry*, vol. 69, No. 6, Mar. 15, 1997, pp. 1174–1178.

Salimi–Moosavi, H., et al., "Electroosmotic Pumping of Organic Solvents and Reagents in Microfabricated Reactor Chips," *Journal of Americal Chemical Society*, vol. 119, No. 37, 1997, pp. 8716–8717.

Xue, Q., et al., "Multichannel Microchip Electrospray Mass Spectrometry," *Analytical Chemistry*, vol. 69, No. 3, Feb. 1, 1997, pp. 426–430.

*Primary Examiner*—Kiet T. Nguyen
(74) *Attorney, Agent, or Firm*—Christenson O'Connor Johnson Kindness PLLC

(57) ABSTRACT

The present invention provides a electroosmotic fluidic device and method for delivering analytes to an analyzer to obtain structural information for the analyte. The device and method are useful in identifying proteins by mass spectrometry.

14 Claims, 19 Drawing Sheets

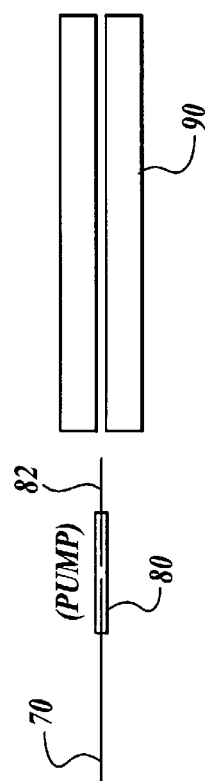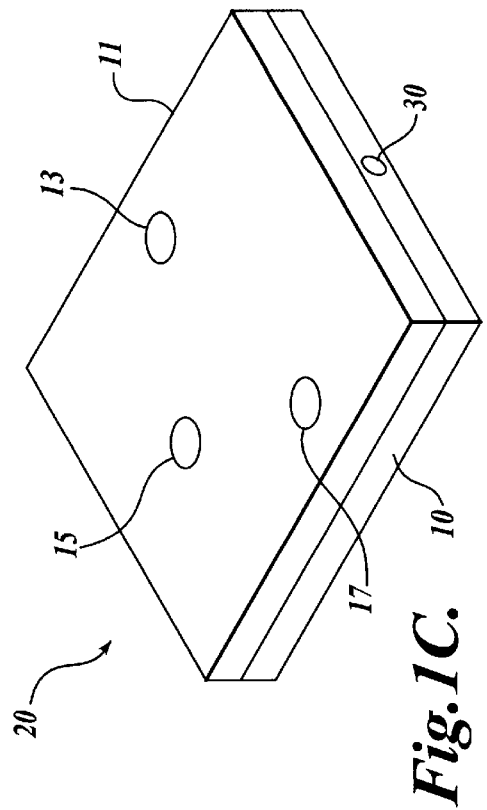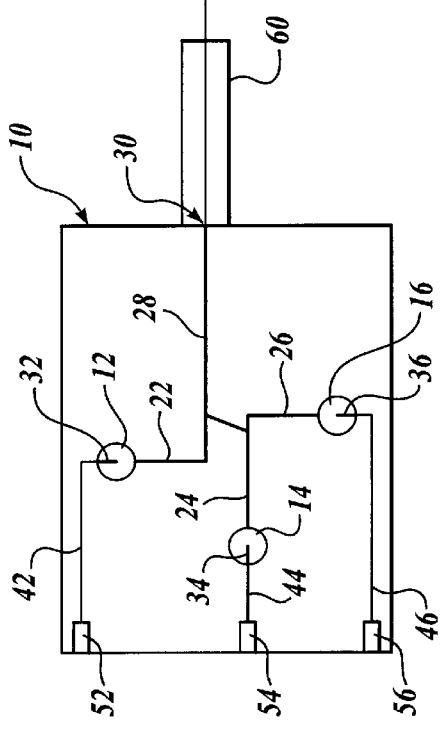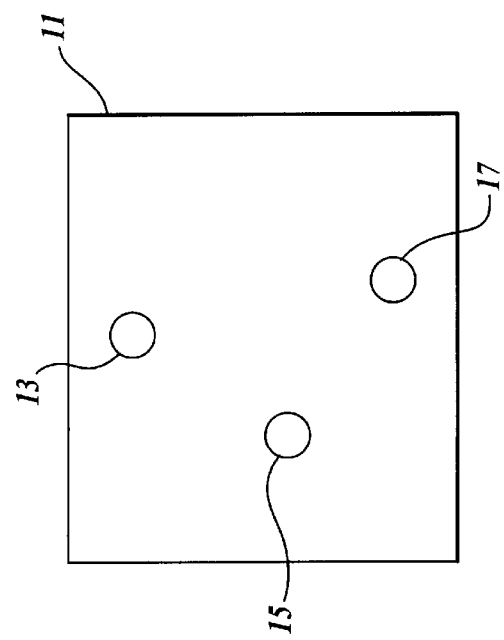
Fig.1A.
Fig.1C.
Fig.1B.

SEQUENCE LISTING

<160> NUMBER OF SEQ ID NOS: 66

<210> SEQ ID NO 1
<211> LENGTH: 11
<212> TYPE: PRT
<213> ORGANISM: Saccharomyces cerevisiae

<400> SEQUENCE: 1

Lys Val Gly Asp Ala Asn Pro Ala Leu Gln Lys
1               5                   10

<210> SEQ ID NO 2
<211> LENGTH: 10
<212> TYPE: PRT
<213> ORGANISM: Saccharomyces cerevisiae

<400> SEQUENCE: 2

Lys Asp Phe Pro Ile Ala Asn Gly Glu Arg
1               5                   10

<210> SEQ ID NO 3
<211> LENGTH: 13
<212> TYPE: PRT
<213> ORGANISM: Saccharomyces cerevisiae

<400> SEQUENCE: 3

```
Lys Glu Pro Ile Ser Val Ser Ser Gln Gln Met Leu Lys
1               5                   10
```

<210> SEQ ID NO 4
<211> LENGTH: 8
<212> TYPE: PRT
<213> ORGANISM: Saccharomyces cerevisiae

<400> SEQUENCE: 4

```
Leu Asp Ala Leu Asp Ser Ile Lys
1               5
```

<210> SEQ ID NO 5
<211> LENGTH: 9
<212> TYPE: PRT
<213> ORGANISM: Saccharomyces cerevisiae

<400> SEQUENCE: 5

```
Val Leu Asp Ala Leu Asp Ser Ile Lys
1               5
```

<210> SEQ ID NO 6
<211> LENGTH: 10
<212> TYPE: PRT
<213> ORGANISM: Saccharomyces cerevisiae

<400> SEQUENCE: 6

```
Val Gly Asp Ala Asn Pro Ala Leu Gln Lys
1               5                   10
```

<210> SEQ ID NO 7
<211> LENGTH: 10
<212> TYPE: PRT
<213> ORGANISM: Saccharomyces cerevisiae

<400> SEQUENCE: 7

```
Lys Val Leu Asp Ala Leu Asp Ser Ile Lys
1               5                   10
```

<210> SEQ ID NO 8
<211> LENGTH: 11
<212> TYPE: PRT
<213> ORGANISM: Saccharomyces cerevisiae

<400> SEQUENCE: 8

```
Asp Gly Leu Ala Val Val Gly Val Phe Leu Lys
1               5                   10
```

<210> SEQ ID NO 9
<211> LENGTH: 22
<212> TYPE: PRT
<213> ORGANISM: Saccharomyces cerevisiae

<400> SEQUENCE: 9

```
Lys Ala Val Val Gln Asp Pro Ala Leu Lys Pro Leu Ala Leu Val Tyr
1               5                   10                  15

Gly Glu Ala Thr Ser Arg
            20
```

<210> SEQ ID NO 10
<211> LENGTH: 23
<212> TYPE: PRT
<213> ORGANISM: Saccharomyces cerevisiae

<400> SEQUENCE: 10

```
Lys Tyr Gly Asp Phe Gly Thr Ala Ala Gln Gln Pro Asp Gly Leu Ala
1               5                   10                  15

Val Val Gly Val Phe Leu Lys
            20
```

<210> SEQ ID NO 11
<211> LENGTH: 13
<212> TYPE: PRT
<213> ORGANISM: Saccharomyces cerevisiae

<400> SEQUENCE: 11

```
Gln Pro Asp Gly Leu Ala Val Val Gly Val Phe Leu Lys
1               5                   10
```

<210> SEQ ID NO 12
<211> LENGTH: 13
<212> TYPE: PRT
<213> ORGANISM: Saccharomyces cerevisiae

<400> SEQUENCE: 12

```
Lys Pro Leu Ala Leu Val Tyr Gly Glu Ala Thr Ser Arg
1               5                   10
```

<210> SEQ ID NO 13
<211> LENGTH: 14
<212> TYPE: PRT
<213> ORGANISM: Saccharomyces cerevisiae

<400> SEQUENCE: 13

```
Arg Thr Leu Asn Phe Asn Ala Glu Gly Glu Pro Glu Leu Leu
1               5                   10
```

<210> SEQ ID NO 14
<211> LENGTH: 16
<212> TYPE: PRT
<213> ORGANISM: Saccharomyces cerevisiae

<400> SEQUENCE: 14

```
Lys Ser Thr Asp Phe Pro Asn Phe Asp Pro Gly Ser Leu Leu Pro Asn
1               5                   10                  15
```

<210> SEQ ID NO 15
<211> LENGTH: 16
<212> TYPE: PRT
<213> ORGANISM: Saccharomyces cerevisiae

<400> SEQUENCE: 15

```
Arg Thr Leu Asn Phe Asn Ala Glu Gly Glu Pro Glu Leu Leu Met Leu
1               5                   10                  15
```

<210> SEQ ID NO 16
<211> LENGTH: 10
<212> TYPE: PRT
<213> ORGANISM: Saccharomyces cerevisiae

<400> SEQUENCE: 16

```
Arg Gln Ser Pro Val Asn Ile Asp Thr Lys
1               5                   10
```

<210> SEQ ID NO 17
<211> LENGTH: 11
<212> TYPE: PRT
<213> ORGANISM: Saccharomyces cerevisiae -continued

```
<400> SEQUENCE: 17

Leu Ala Leu Val Tyr Gly Glu Ala Thr Ser Arg
1               5                   10

<210> SEQ ID NO 18
<211> LENGTH: 12
<212> TYPE: PRT
<213> ORGANISM: Saccharomyces cerevisiae

<400> SEQUENCE: 18

Lys Ala Val Val Gln Asp Pro Ala Leu Lys Pro Leu
1               5                   10

<210> SEQ ID NO 19
<211> LENGTH: 19
<212> TYPE: PRT
<213> ORGANISM: Saccharomyces cerevisiae

<400> SEQUENCE: 19

Arg Met Val Asn Asn Gly His Ser Phe Asn Val Glu Tyr Asp Asp Ser
1               5                   10                  15

Gln Asp Lys

<210> SEQ ID NO 20
<211> LENGTH: 11
<212> TYPE: PRT
<213> ORGANISM: Saccharomyces cerevisiae

<400> SEQUENCE: 20

Lys Leu Val Asn Glu Leu Thr Glu Phe Ala Lys
1               5                   10

<210> SEQ ID NO 21
<211> LENGTH: 11
<212> TYPE: PRT
<213> ORGANISM: Saccharomyces cerevisiae

<400> SEQUENCE: 21

Arg Phe Lys Asp Leu Gly Glu Glu His Phe Lys
1               5                   10

<210> SEQ ID NO 22
<211> LENGTH: 12
<212> TYPE: PRT
<213> ORGANISM: Saccharomyces cerevisiae

<400> SEQUENCE: 22

Lys His Leu Val Asp Glu Pro Gln Asn Leu Ile Lys
1               5                   10

<210> SEQ ID NO 23
<211> LENGTH: 14
<212> TYPE: PRT
<213> ORGANISM: Saccharomyces cerevisiae

<400> SEQUENCE: 23

Lys Leu Gly Glu Tyr Gly Phe Gln Asn Ala Leu Ile Val Arg
1               5                   10

<210> SEQ ID NO 24
<211> LENGTH: 16
<212> TYPE: PRT
<213> ORGANISM: Saccharomyces cerevisiae
```

<400> SEQUENCE: 24

Arg Lys Val Pro Gln Val Ser Thr Pro Thr Leu Val Glu Val Ser Arg
1               5                   10                  15

<210> SEQ ID NO 25
<211> LENGTH: 16
<212> TYPE: PRT
<213> ORGANISM: Saccharomyces cerevisiae

<400> SEQUENCE: 25

Arg His Pro Tyr Phe Tyr Ala Pro Glu Leu Leu Tyr Tyr Ala Asn Lys
1               5                   10                  15

<210> SEQ ID NO 26
<211> LENGTH: 17
<212> TYPE: PRT
<213> ORGANISM: Saccharomyces cerevisiae

<400> SEQUENCE: 26

Arg Arg His Pro Tyr Phe Tyr Ala Pro Glu Leu Leu Tyr Tyr Ala Asn
1               5                   10                  15

Lys

<210> SEQ ID NO 27
<211> LENGTH: 14
<212> TYPE: PRT
<213> ORGANISM: Saccharomyces cerevisiae

<400> SEQUENCE: 27

Lys Asp Ala Phe Leu Gly Ser Phe Leu Tyr Glu Tyr Ser Arg
1               5                   10

<210> SEQ ID NO 28
<211> LENGTH: 11
<212> TYPE: PRT
<213> ORGANISM: Saccharomyces cerevisiae

<400> SEQUENCE: 28

Arg Val Val Asp Leu Ile Glu Tyr Val Ala Lys
1               5                   10

<210> SEQ ID NO 29
<211> LENGTH: 12
<212> TYPE: PRT
<213> ORGANISM: Saccharomyces cerevisiae

<400> SEQUENCE: 29

Arg Asp Pro Ala Asn Leu Pro Trp Gly Ser Leu Lys
1               5                   10

<210> SEQ ID NO 30
<211> LENGTH: 15
<212> TYPE: PRT
<213> ORGANISM: Saccharomyces cerevisiae

<400> SEQUENCE: 30

Arg Val Pro Thr Val Asp Val Ser Val Val Asp Leu Thr Val Lys
1               5                   10                  15

<210> SEQ ID NO 31
<211> LENGTH: 18
<212> TYPE: PRT
<213> ORGANISM: Saccharomyces cerevisiae

```
<400> SEQUENCE: 31

Lys Val Ile Asn Asp Ala Phe Gly Ile Glu Glu Gly Leu Met Thr Thr
1               5                   10                  15

Val His

<210> SEQ ID NO 32
<211> LENGTH: 25
<212> TYPE: PRT
<213> ORGANISM: Saccharomyces cerevisiae

<400> SEQUENCE: 32

Lys Val Ile Asn Asp Ala Phe Gly Ile Glu Glu Gly Leu Met Thr Thr
1               5                   10                  15

Val His Ser Met Thr Ala Thr Gln Lys
            20                  25

<210> SEQ ID NO 33
<211> LENGTH: 24
<212> TYPE: PRT
<213> ORGANISM: Saccharomyces cerevisiae

<400> SEQUENCE: 33

Lys Asp Pro Ala Asn Leu Pro Trp Gly Ser Ser Asn Val Asp Ile Ala
1               5                   10                  15

Ile Asp Ser Thr Gly Val Phe Lys
            20

<210> SEQ ID NO 34
<211> LENGTH: 24
<212> TYPE: PRT
<213> ORGANISM: Saccharomyces cerevisiae

<400> SEQUENCE: 34

Lys Pro Asn Val Glu Val Val Ala Leu Asn Asp Pro Phe Thr Thr Asn
1               5                   10                  15

Asp Tyr Ala Ala Tyr Met Phe Lys
            20

<210> SEQ ID NO 35
<211> LENGTH: 25
<212> TYPE: PRT
<213> ORGANISM: Saccharomyces cerevisiae

<400> SEQUENCE: 35

Lys Val Ile Asn Asp Ala Phe Gly Ile Glu Glu Gly Leu Met Thr Thr
1               5                   10                  15

Val His Ser Leu Thr Ala Thr Gln Lys
            20                  25

<210> SEQ ID NO 36
<211> LENGTH: 22
<212> TYPE: PRT
<213> ORGANISM: Saccharomyces cerevisiae

<400> SEQUENCE: 36

Lys Val Val Ile Thr Ala Pro Ser Ser Thr Ala Pro Met Phe Val Met
1               5                   10                  15

Gly Val Asn Glu Glu Lys
            20
```

```
<210> SEQ ID NO 37
<211> LENGTH: 15
<212> TYPE: PRT
<213> ORGANISM: Saccharomyces cerevisiae

<400> SEQUENCE: 37

Lys Leu Val Ser Trp Tyr Asp Asn Glu Tyr Gly Tyr Ser Thr Arg
1               5                   10                  15

<210> SEQ ID NO 38
<211> LENGTH: 15
<212> TYPE: PRT
<213> ORGANISM: Saccharomyces cerevisiae

<400> SEQUENCE: 38

Ser Ser Thr Ala Pro Met Phe Val Met Gly Val Asn Glu Glu Lys
1               5                   10                  15

<210> SEQ ID NO 39
<211> LENGTH: 13
<212> TYPE: PRT
<213> ORGANISM: Saccharomyces cerevisiae

<400> SEQUENCE: 39

Lys Glu Glu Thr Leu Asn Pro Ile Ile Gln Asp Thr Lys
1               5                   10

<210> SEQ ID NO 40
<211> LENGTH: 18
<212> TYPE: PRT
<213> ORGANISM: Saccharomyces cerevisiae

<400> SEQUENCE: 40

Lys Ile Pro Asp Gly Lys Pro Glu Asn Gln Phe Ala Phe Ser Gly Glu
1               5                   10                  15

Ala Lys

<210> SEQ ID NO 41
<211> LENGTH: 18
<212> TYPE: PRT
<213> ORGANISM: Saccharomyces cerevisiae

<400> SEQUENCE: 41

Lys Leu Glu Ile Thr Lys Glu Glu Thr Leu Asn Pro Ile Ile Gln Asp
1               5                   10                  15

Thr Lys

<210> SEQ ID NO 42
<211> LENGTH: 14
<212> TYPE: PRT
<213> ORGANISM: Saccharomyces cerevisiae

<400> SEQUENCE: 42

Lys Val Ile Ala Ile Asp Ile Asn Asp Pro Leu Ala Pro Lys
1               5                   10

<210> SEQ ID NO 43
<211> LENGTH: 18
<212> TYPE: PRT
<213> ORGANISM: Saccharomyces cerevisiae

<400> SEQUENCE: 43

Lys Gly Ile Asp Leu Thr Asn Val Thr Leu Pro Asp Thr Pro Thr Tyr
```

```
                1               5              10              15

Ser Lys

<210> SEQ ID NO 44
<211> LENGTH: 14
<212> TYPE: PRT
<213> ORGANISM: Saccharomyces cerevisiae

<400> SEQUENCE: 44

Lys Glu Asn Asn Ile Phe Asn Met Val Val Glu Ile Pro Arg
1               5                  10

<210> SEQ ID NO 45
<211> LENGTH: 25
<212> TYPE: PRT
<213> ORGANISM: Saccharomyces cerevisiae

<400> SEQUENCE: 45

Lys Ala Val Gly Asp Asn Asp Pro Ile Asp Val Leu Glu Ile Gly Glu
1               5                  10                  15

Thr Ile Ala Tyr Thr Gly Gln Val Lys
            20                  25

<210> SEQ ID NO 46
<211> LENGTH: 12
<212> TYPE: PRT
<213> ORGANISM: Saccharomyces cerevisiae

<400> SEQUENCE: 46

Arg Gly Phe Leu Ser Asp Leu Pro Asp Phe Glu Lys
1               5                  10

<210> SEQ ID NO 47
<211> LENGTH: 13
<212> TYPE: PRT
<213> ORGANISM: Saccharomyces cerevisiae

<400> SEQUENCE: 47

Lys Thr Ser Phe Phe Gln Ala Leu Gly Val Pro Thr Lys
1               5                  10

<210> SEQ ID NO 48
<211> LENGTH: 20
<212> TYPE: PRT
<213> ORGANISM: Saccharomyces cerevisiae

<400> SEQUENCE: 48

Lys Ser Leu Phe Val Val Gly Val Asp Asn Val Ser Ser Gln Gln Met
1               5                  10                  15

His Glu Val Arg
            20

<210> SEQ ID NO 49
<211> LENGTH: 13
<212> TYPE: PRT
<213> ORGANISM: Saccharomyces cerevisiae

<400> SEQUENCE: 49

Arg Ala Gly Ala Val Ala Pro Glu Asp Ile Trp Val Arg
1               5                  10

<210> SEQ ID NO 50
<211> LENGTH: 11
```

```
<212> TYPE: PRT
<213> ORGANISM: Saccharomyces cerevisiae

<400> SEQUENCE: 50

Arg Gly Thr Ile Glu Ile Val Ser Asp Val Lys
1               5                   10

<210> SEQ ID NO 51
<211> LENGTH: 18
<212> TYPE: PRT
<213> ORGANISM: Saccharomyces cerevisiae

<400> SEQUENCE: 51

Lys Thr Ala Ser Glu Ile Ala Thr Thr Glu Leu Pro Pro Thr His Pro
1               5                   10                  15

Ile Arg

<210> SEQ ID NO 52
<211> LENGTH: 13
<212> TYPE: PRT
<213> ORGANISM: Saccharomyces cerevisiae

<400> SEQUENCE: 52

Arg Phe Leu Glu Gln Gln Asn Gln Val Leu Gln Thr Lys
1               5                   10

<210> SEQ ID NO 53
<211> LENGTH: 16
<212> TYPE: PRT
<213> ORGANISM: Saccharomyces cerevisiae

<400> SEQUENCE: 53

Lys Gln Ile Ser Asn Leu Gln Gln Ser Ile Ser Asp Ala Glu Gln Arg
1               5                   10                  15

<210> SEQ ID NO 54
<211> LENGTH: 13
<212> TYPE: PRT
<213> ORGANISM: Saccharomyces cerevisiae

<400> SEQUENCE: 54

Arg Leu Asn Asp Leu Glu Asp Ala Leu Gln Gln Ala Lys
1               5                   10

<210> SEQ ID NO 55
<211> LENGTH: 13
<212> TYPE: PRT
<213> ORGANISM: Saccharomyces cerevisiae

<400> SEQUENCE: 55

Lys Ser Leu Asn Asn Gln Phe Ala Ser Phe Ile Asp Lys
1               5                   10

<210> SEQ ID NO 56
<211> LENGTH: 30
<212> TYPE: PRT
<213> ORGANISM: Saccharomyces cerevisiae

<400> SEQUENCE: 56

Lys Asp Ile Glu Asn Gln Tyr Glu Thr Gln Ile Thr Gln Ile Glu His
1               5                   10                  15

Glu Val Ser Ser Ser Gly Gln Glu Val Gln Ser Ser Ala Lys
                20                  25                  30
```

<210> SEQ ID NO 57
<211> LENGTH: 21
<212> TYPE: PRT
<213> ORGANISM: Saccharomyces cerevisiae

<400> SEQUENCE: 57

Lys Leu Gly Glu His Asn Ile Asp Val Leu Glu Gly Asn Glu Gln Phe
1               5                   10                  15

Ile Asn Ala Ala Lys
            20

<210> SEQ ID NO 58
<211> LENGTH: 9
<212> TYPE: PRT
<213> ORGANISM: Saccharomyces cerevisiae

<400> SEQUENCE: 58

Lys Ile Asn Glu Gly Ile Leu Gln Arg
1               5

<210> SEQ ID NO 59
<211> LENGTH: 19
<212> TYPE: PRT
<213> ORGANISM: Saccharomyces cerevisiae

<400> SEQUENCE: 59

Lys Asp Thr Leu Pro Leu Gly Phe Thr Thr Phe Ser Tyr Pro Ala Ser
1               5                   10                  15

Gln Asn Lys

<210> SEQ ID NO 60
<211> LENGTH: 24
<212> TYPE: PRT
<213> ORGANISM: Saccharomyces cerevisiae

<400> SEQUENCE: 60

Lys Gly Phe Asp Ile Ile Pro Asn Val Glu Gly His Asp Val Val Pro
1               5                   10                  15

Leu Leu Gln Asn Glu Ile Ser Lys
            20

<210> SEQ ID NO 61
<211> LENGTH: 8
<212> TYPE: PRT
<213> ORGANISM: Saccharomyces cerevisiae

<400> SEQUENCE: 61

Lys Ser Leu Gly Ile Ile Gly Ala
1               5

<210> SEQ ID NO 62
<211> LENGTH: 18
<212> TYPE: PRT
<213> ORGANISM: Saccharomyces cerevisiae

<400> SEQUENCE: 62

Arg Leu Gly Glu His Asn Ile Asp Val Leu Glu Gly Asn Glu Gln Phe
1               5                   10                  15

Ile Asn

<210> SEQ ID NO 63
<211> LENGTH: 20

```
<212> TYPE: PRT
<213> ORGANISM: Saccharomyces cerevisiae
<220> FEATURE:
<221> NAME/KEY: -
<222> LOCATION: (18)..(18)
<223> OTHER INFORMATION: Xaa = methyl methionine

<400> SEQUENCE: 63

Lys Ile Ile Thr His Pro Asn Phe Asn Gly Asn Thr Leu Asp Asn Asp
1               5                   10                  15

Ile Xaa Ile Lys
            20

<210> SEQ ID NO 64
<211> LENGTH: 21
<212> TYPE: PRT
<213> ORGANISM: Saccharomyces cerevisiae

<400> SEQUENCE: 64

Lys Ile Ile Thr His Pro Asn Phe Asn Gly Asn Thr Leu Asp Asn Asp
1               5                   10                  15

Ile Met Leu Ile Lys
            20

<210> SEQ ID NO 65
<211> LENGTH: 21
<212> TYPE: PRT
<213> ORGANISM: Saccharomyces cerevisiae

<400> SEQUENCE: 65

Arg Leu Gly Glu His Asn Ile Asp Val Leu Glu Gly Asn Glu Gln Phe
1               5                   10                  15

Ile Asn Ala Ala Lys
            20

<210> SEQ ID NO 66
<211> LENGTH: 13
<212> TYPE: PRT
<213> ORGANISM: Saccharomyces cerevisiae

<400> SEQUENCE: 66

Arg Phe Leu Glu Gln Gln Asn Gln Val Leu Gln Thr Lys
1               5                   10
```

ELECTROOSMOTIC FLUIDIC DEVICE AND RELATED METHODS

CROSS-REFERENCE TO RELATED APPLICATION

This application is a continuation of U.S. application Ser. No. 09/209,880, filed Dec. 11, 1998, which claims the benefit of U.S. Provisional Application No. 60/069,398, filed Dec. 12, 1997.

This invention was made in part with government support under grant T32HG00035-3 awarded by the National Institutes' of Health and grant BIR9214821AM04 awarded by the National Science Foundation. The government has certain rights in the invention.

FIELD OF THE INVENTION

The present invention relates to a device and method for directing analytes to an analyzer and, more particularly, to a fluidic device and method that directs analytes to a mass spectrometer through electroosmotic pumping.

BACKGROUND OF THE INVENTION

A protein can be conclusively identified, without the need for de novo sequence determination, by correlating the information contained in its amino acid sequence with the corresponding object in a sequence database. The rapidly growing size of genomic, cDNA, and expressed sequence tag sequence databases has made this approach increasingly valuable. Several methods differing in the type of information extracted from the protein sample and the degree of automation have been described. The most conclusive and reliable methods are based on correlating collision-induced dissociation (CID) mass spectra of peptides with sequence databases. CID spectra of peptides are most frequently generated by electrospray ionization tandem mass spectrometry (ESI-MS/MS) on triple quadrupole or ion trap mass spectrometers.

For the generation of CID spectra in ESI systems, peptide samples have been introduced into the mass spectrometer by continuous infusion (flow injection) or on-line from liquid chromatography (LC) or capillary electrophoresis (CE) systems. The development of micro- and nano-electrospray ion sources has significantly improved the limit of detection achievable in ESI-MS to the low femtomole to attomole level. For the purpose of protein identification using peptide CID spectra, micro- and nano-electrospray ionization techniques have been successfully used with techniques to separate the peptides contained in protein digests and also in continuous flow analysis. In the continuous flow mode, the sample is sprayed into the MS at a flow rate of a few nl/min without peptide separation. CID spectra are sequentially generated from selected constituent peptides and used to search sequence databases or for de novo sequence determination. The most sensitive implementation of the continuous flow nanospray method is slow, tedious and difficult to automate and therefore does not realize the potential of the flow injection approach for high sample throughput and automated protein analysis. The methods involving on-line peptide separation have demonstrated the benefits of sample purification from contaminants, resolution of analytes and sample concentration. However, these methods are technically more involved and the most sensitive implementations have been difficult to automate.

The shift from the analysis of single genes and isolated proteins to the comprehensive analysis of biological systems and pathways has been one of the most dramatic recent developments in biological research. The shift is a direct consequence of the development of automated, high throughput genomic technologies which are now used for whole genome sequencing (e.g., *Haemophilus influenzae* Rd and *Saccharomyces cerevisiae*) and for the establishment of comprehensive mRNA expression maps. However, there is currently no equivalent technology available for the analysis of biological systems on the protein level. Because proteins are the most significant class of biological control and effector molecules, a complete model of a biological process cannot be established without knowledge of the identity, function and state of activity of the proteins involved. Therefore, there is a demonstrated need for the development of a technology for the rapid and conclusive identification of proteins.

The current technologies for protein analysis described above have reached a level of sensitivity which permits the identification of essentially any protein which is detectable by conventional protein staining. However, protein sample throughput is orders of magnitude lower than the throughput of DNA-based technologies and some of the most sensitive protein analysis techniques developed to date are difficult to automate.

The implementation of steps required for protein identification by MS/MS (e.g., protein isolation. enzymatic or chemical fragmentation, peptide separation, and delivery of peptides to a mass analyzer) on microfabricated devices is a promising approach to enhance sample throughput and the sensitivity of protein analysis.

Microfabricated devices have been used previously for capillary electrophoresis and capillary gel electrophoresis where the analytes are detected on the device, typically by laser-induced fluorescence providing little structural information. Accordingly, there exists a need for a device and method for analyzing small quantities of proteins and providing structural information for the protein. Preferably, such a device and method is rapid, efficient, and readily automated. The present invention seeks to fulfill this need and provides further related advantages.

SUMMARY OF THE INVENTION

The present invention provides a device and method for delivering analytes to an analyzer to obtain structural information for the analyte. The device and method are useful in identifying proteins by mass spectrometry. The present invention is adaptable to many analytical problems beyond protein analysis that require rapid, unambiguous, automated, and sensitive analysis of complex mixtures of analytes.

In one aspect of the present invention, a device for delivering analytes to an analyzer is provided. The device includes one or more reservoirs connected by channels that direct sample flow to the analyzer. The device's reservoirs can include sample and buffer reservoirs, each of which includes an electrode that is in contact with the liquid sample contained within the reservoir. The electrode is connected to a power supply and, on applying a voltage to a reservoir, mobile analytes contained within the reservoir are directed to an analyzer, for example, a mass analyzer by means of a counterelectrode maintained at a stable electrode. The potential difference between the activated reservoir and the counterelectrode induces electroosmotic flow on the device and from the device. Preferably, the device is coupled to mass spectrometer through an interface, such as a microelectrospray interface, to introduce an analyte into a mass spectrometer for analysis.

In one embodiment, the invention provides a device and method for automating the continuous injection approach to protein identification by providing for the sequential infusion of different peptide samples into an electrospray ionization mass spectrometer without the need for sample manipulation. As noted above, the device includes sample and buffer reservoirs that are etched into the device and connected by channels, which are also etched into the device, and direct the reservoir contents to a microelectrospray ion source. Peptide samples, such as unseparated tryptic digests of proteins, can be applied to different reservoirs. A flow of liquid originating from a specific reservoir can be generated and selectively directed toward the microsprayer and the mass spectrometer by electroosmotic pumping. The analyte proteins can be identified by searching sequence databases either with the peptide masses generated by chemical or enzymatic protein fragmentation or with collision-induced dissociation (CID) spectra of selected peptides. The system achieves a limit of detection in the low fmol/μl range for peptide standards and can conclusively identify proteins at the low fmol/μl level. Furthermore, samples deposited in different reservoirs can be sequentially mobilized and analyzed without cross-contamination.

In another aspect, the present invention provides a system for the automated analysis of multiple analytes such as protein samples. The system includes a fluidics device, preferably a fluidics device such as described above, having multiple sample reservoirs for containing and directing samples to an analyzer; a computer-controlled array of high voltage relays for sequentially mobilizing analytes contained in the reservoirs and electroosmotically pumping the analyte to the analyzer; and an analyzer such as a mass spectrometer for providing structural information for the analyte. In a preferred embodiment, the system includes a fluidics device that is a microfabricated device interfaced with a mass spectrometer, preferably an electrospray ionization tandem mass spectrometer. The system can be used for the sequential automated analysis of protein digests. The system is also useful for the automated identification of proteins separated by gel electrophoresis.

In a further aspect of the present invention, a device for generating and delivering solvent gradients, preferably at nanoliter per minute flow rates, is provided. The device is as described above and includes multiple reservoirs, at least two reservoirs containing different solvents and channels for delivering the generated solvent from the device. The solvent gradient is generated by directed differential electroosmotic pumping from reservoirs on the device that contain different solvents. In one embodiment, the device for generating and delivering the solvent gradient is coupled to a sample, such as a sample of one or more proteins immobilized on a solid phase extraction cartridge, which is, in turn, coupled to an analyzer, preferably a mass spectrometer. The system can be used for frontal analysis of complex peptide mixtures such as protein digests and analysis of separated peptides by mass spectrometry.

BRIEF DESCRIPTION OF THE DRAWINGS

FIG. 1A is a schematic diagram of a representative system formed in accordance with the present invention including a representative three-position fluidics device, capillary electroosmotic pump, and microelectrospray interface coupled to the entrance of a mass spectrometer;

FIG. 1B is a schematic diagram of a cover for the representative three-position fluidics device illustrated in FIG. 1A;

FIG. 1C is a schematic diagram for a representative three-position fluidic device of the present invention;

FIG. 7A is a graph of signal-to-background ratio in MS mode for 3 peptides from β-lactoglobulin (βlac) digest plotted against analyte concentrations (log scale); FIG. 7B is a graph of cross correlation factor (Xcorr) from Sequest database searches for βlac peptides plotted against analyte concentration (log scale);

FIG. 8A is the mass spectrum obtained for BSA tryptic digest flowing from reservoir 1 at 182 fmol/μl; FIG. 8B is the mass spectrum obtained for horse myoglobin tryptic digest from reservoir 2 at 237 fmol/μl; and FIG. 8C is the mass spectrum obtained for human haptoglobin tryptic digest from reservoir 3 at 222 fmol/μl;

FIG. 13A illustrates the gradient operated with an uncoated transfer capillary and FIG. 13B illustrates the gradient generated with a (3-aminopropyl)silane-coated capillary;

DETAILED DESCRIPTION OF THE INVENTION

Figure 2A:
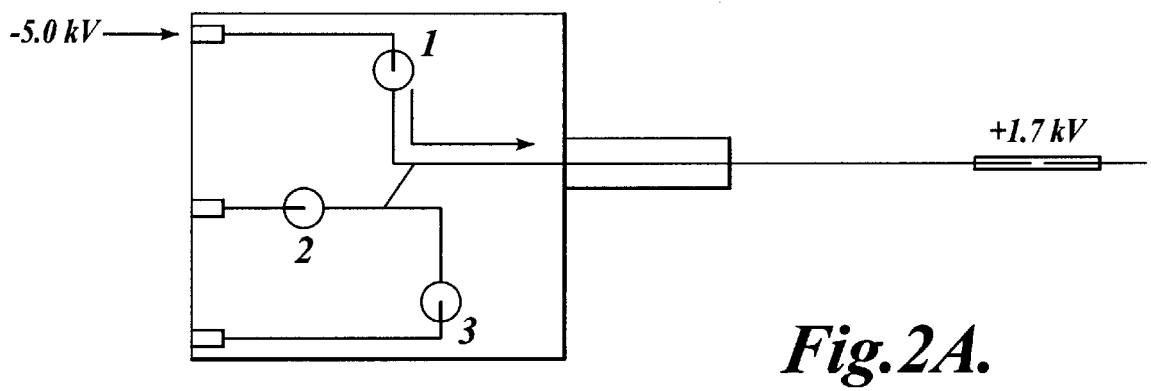
FIGS. 2A, 2B, and 2C are flow diagrams illustrating representative methods of the present invention.

The present invention provides a fluidic device for directing liquid flow through electroosmotic pumping. Methods of the invention provide for liquid flow on the device and from the device to an analytical instrument, for example, a mass analyzer.

In one aspect of the invention, analytes deposited on the device are selectively delivered to an analyzer. In another aspect, the invention provides a device for generating and delivering a solvent gradient. The device can be coupled to a mass analyzer through an electrospray ionization interface to provide, in another aspect of the invention, a system that can be automated and useful in the identification of analytes such as peptides and proteins. Methods for selectively delivering analytes to an analyzer, generating and delivering solvent gradients, and identifying proteins by mass spectrometry using the fluidic device are also provided by the invention.

In one aspect, the present invention provides a fluidic device for delivering an analyte to an analyzer. In one embodiment, the analyte is deposited or immobilized on the device and, in another embodiment, the analyte is immobilized downstream from the device between the device and the analyzer. Preferably, the fluidic device is a microfabricated device and the analyzer is a mass spectrometer.

The device includes at least one reservoir, preferably three or more reservoirs, and one or more channels for directing liquid flow from the reservoir or reservoirs and from the device to, for example, an analyzer. For devices having multiple reservoirs, a channel directs liquid flow from each reservoir to a channel that directs flow from the device. Generally, the channel directing flow from the device is coupled to a transfer capillary which directs flow to, for example, an electrospray ionization interface and a mass spectrometer. Preferably, the device's reservoirs and channels are etched or molded into the device.

The device of the invention directs flow by electroosmotic pumping. To effect electroosmotic pumping, each reservoir includes an electrode in contact with liquid contained within the reservoir. The potential difference created by applying a potential to one or more electrodes of the device and a counterelectrode, for example, an electrospray ionization source needle, results in electroosmotic pumping of liquid and/or analytes from the reservoir through the channel to the ionization source.

A representative fluid device of the present invention having three reservoirs (i.e., a three-position device) is shown in FIG. 1A. Referring to FIG. 1A, device 10 includes reservoirs 12, 14, and 16 connected by channels 22, 24, and 26. The dimensions of the reservoirs and channels are not critical. Preferably, the channels have a width from about 5 $\mu$m to about 100 $\mu$m, and a depth from about 5 $\mu$m to about 100 $\mu$m. Reservoirs 12, 14, and 16 include electrodes 32, 34, and 36, respectively, which are connected by leads 42, 44, and 46 to contact pads 52, 54, and 56, respectively. Depending on the applied potential, liquid and/or analytes can be selectively migrated from reservoirs 12, 14, or 16 through channels 22, 24, or 26, respectively, through channel 28 and from device 10 through fluid exit 30 to transfer capillary 70 coupled to device 10 by fitting 60. Transfer capillary 70 terminates in liquid junction 80 which includes electrospray needle 82 and forms an interface to a mass spectrometer.

The length of the transfer capillary can be varied and, in one embodiment, the electrospray needle is connected directly to the fluidic device without a capillary.

The fluidic device of the invention can include an overlying cover. The cover can be formed from the same or different material used to form device's base into which the reservoir(s) and channels are etched. The cover includes apertures that permit the introduction of samples to the device's reservoir(s). Referring to FIG. 1B, representative cover 11 has a surface area about that of device 10 and includes apertures 13, 15, and 17 coincident with reservoirs 12, 14, and 16, respectively, when cover 11 is attached to device 10. A representative device of the invention having a cover as illustrated in FIG. 1B is shown in FIG. 1C. Referring to FIG. 1C, device 20 includes cover 11 attached to device 10. Apertures 13, 15, and 17 and fluid exit 30 are also indicated in the figure.

In a preferred embodiment, the device is a microfabricated device. Briefly, channels 22, 24, and 26 (30 $\mu$m depth×72–73 $\mu$m width) and reservoirs 12, 14, and 16 (2 mm×2 mm×30 $\mu$m depth) were etched on a piece of glass (540 $\mu$m thick) as indicated in FIG. 1A. A photomask representing the etching pattern was obtained from Precision Photomask (Montreal, QB, Canada). The etching was done with an isotropic process using hydrofluoric acid. Onto each reservoir, 60 nm thick gold electrodes 32, 34, and 36 were vacuum deposited. A 10 nm thick vacuum deposited nickel chromium (NiCr) film was used as an adhesion layer between the gold and the glass substrate. The electrodes in reservoirs had dimensions of about 0.4 mm×1.0 mm. Electrodes 32, 34, and 36 were connected to 1 mm×2 mm contact pads 52, 54, and 56, respectively, by 80 $\mu$m wide metal lines 42, 44, and 46, respectively. The contact pad is used to apply high voltage. On a second piece of glass (540 $\mu$m thick), holes (1.8 mm in diameter) were drilled through the glass at the positions of the reservoirs using a carbide bit. The glass pieces were aligned and bonded at a temperature above the annealing point and below the melting point of the glass. To increase sample volume, an extension is optionally added over each reservoir by gluing in place a pipette tip.

The device of the present invention can be formed from a variety of materials including glass materials, such as quartz, and plastic materials. Generally, any relatively chemically inert and nonconducting material into which reservoirs and channels can be etched or formed is suitable. In addition to glass materials, suitable materials include hard plastic materials, such as polypropylene, that can be etched by laser or chemical processes. Alternatively, the device can be formed by molding processes. For molded embodiments, the device is preferably formed from soft plastic materials including, for example, polydimethylsiloxane (PDMS), polyurethane, and epoxy (e.g., Tra-Bond F113, commercially available from Tra-Con Inc.). In a preferred embodiment, the molded device is formed from polydimethylsiloxane.

As noted above, the fluidic device can be coupled to an analyzer through an electrosprayer. Device 10 was connected to microsprayer 82 through a 12 cm piece of 75 µm inner diameter (i.d.)×150 µm outer diameter (o.d.) fused silica capillary tubing 70 which was derivatized on the inner surface with 3-aminopropylsilane. Non-derivatized capillaries can also be used. In this embodiment, the capillary serves as an electroosmotic pump. The flow rate can be adjusted and controlled by the electric field and the i.d. and length of the capillary. The link between device 10 and the capillary 70 can be made by gluing a 1.6 mm i.d.×3.2 mm o.d. TEFLON sleeve 60 to the edge of the device. A second TEFLON sleeve having a 250 µm i.d.×1.6 mm o.d. was inserted into the first sleeve until contact with the device was made. Finally, the capillary is inserted into the inner TEFLON sleeve until the capillary is cleanly aligned with channel 22 of device 10. The whole assembly is held in place and stabilized by a TEFLON tube-dual shrink placed over the two TEFLON sleeves. The microspray ion source was constructed essentially as previously described. (See, Figeys, D., Ducret, A., III, J. R. Y., Aebersold, R. *Nature Biotech.*, 14:1579–1583 (1996); Figeys, D., Aebersold, R. *Electrophoresis*, 18:360–368 (1997); Figeys, D., Ducret, A., Aebersold, R. *J Chromatogr. A*, 763:295–306 (1997)). The end of capillary 70 was inserted into a piece of stainless steel tubing 82 and held in place with TEFLON tube-dual shrink. A 3 cm portion of 50 µm i.d. capillary was inserted at the other end of the stainless steel tubing and held in place with TEFLON tube-dual shrink and to provide liquid junction 80. The polyimide coat at the end of the 50 µm i.d. tubing directed towards the mass spectrometer entrance was removed before the capillary was introduced into the stainless steel tube. The power supply from the mass spectrometer was connected to the stainless steel tubing and +1.7 to +1.9 kV was applied to generate the microelectrospray. In general, the voltage applied to the counterelectrode (e.g., the electrospray needle) is in the range from about +1.5 to about +2.0 kV.

The operation of the fluidic device coupled to the mass spectrometer as described above is illustrated as follows. Initially, all the reservoirs, channels and capillaries were filled with buffer (10 mM acetic acid pH 3.0 and 10%(v/v) methanol) by applying positive pressure to one of the glued expansions of the reservoirs or by applying vacuum at the microsprayer end. Buffer was then electroosmotically pumped towards the mass spectrometer and the microsprayer was aligned with the entrance of the mass spectrometer using an XYZ translation stage. After the microsprayer alignment, buffer was removed from the sample reservoirs and replaced with sample solutions by using a micropipette. Stock solutions of the samples (e.g., peptide solutions) that had been previously diluted in 10 mM acetic acid and 10%(v/v) methanol were mobilized by applying a negative high voltage to the respective reservoir and a positive high voltage to the microelectrosprayer. For sequential mobilization of samples concurrently present on the device, a method such as illustrated in FIG. 2 can be used. The samples were selectively electrosprayed continuously into the mass spectrometer and mass spectra containing all the positive ions present in the sample having an intensity exceeding a predetermined threshold were generated. Each ion detectable in the spectrum was further selected for collision-induced dissociation (CID). The CID spectra generated were used to search protein databases.

After the first sample was electrosprayed into the mass spectrometer and spectra generated, the next sample was mobilized and flowed into the mass spectrometer and analyzed.

As described above, protein samples immobilized on the device can be selectively mobilized and analyzed by mass spectrometry. The device of the present invention can be interfaced with an electrospray ionization mass spectrometer including, for example, an ion trap mass spectrometer (ITMS). In the following representative method for identifying protein analytes, the trap was run with automatic gain control for all experiments. In this mode, the system automatically selects the trapping parameters to maintain the number of ions present in the trap to a constant preset value. The target number of ions was set to $5 \times 10^7$ in MS mode, and to $2 \times 10^7$ in CID mode. The electron multiplier was set to −850V. In MS mode, the trap was scanned in 3 microscans and 10 scans were averaged. In CID mode, the trap was filled for up to 3 seconds, depending on the number of ions entering the trap per unit of time. Different dissociation energies were used to obtain optimal MS/MS spectra. Data from up to 15 individual spectra were accumulated and averaged depending on the quality of each spectrum.

To establish the identity of proteins, sequence databases were searched with the CID spectra obtained from individual peptide ions using the Sequest software system.

In another aspect, the present invention provides a system for sequentially mobilizing and analyzing peptide samples with minimal cross-contamination. Referring to FIG. 1A, the system includes a fluidic device containing the channels, sample reservoirs and electrodes, a fused silica connection and the microelectrospray ion source. In the system, analytes are brought from the reservoirs to the mass spectrometer using electroosmotic pumping. The inner surface of the 12 cm fused silica capillary tube is preferably derivatized using 3-aminopropylsilane as noted above. At pH 3.0, the permanent positive charge generates a strong electroosmotic flow toward the anode. The channel walls on the device were not derivatized and, at pH 3.0, a small electroosmotic flow towards the anode is generated. The main portion of the total electroosmotic flow was generated by capillary tube 70 which is designated "pump" in FIG. 1A. The differential in electroosmotic pumping between the device and the capillary tube pump requires a tight seal at the interface. The equilibrium liquid flow through the device is established by viscous drag of the liquid. Because the dimensions of the etched channels are different from the dimension of the capillary tube pump, different linear flow velocities are generated on the device and in the capillary. A volume flow rate of 200 nl/min was obtained with −4 kV applied to reservoir 1 and +1.7 kV applied to the microelectrospray. In general, the voltage applied to the device's electrodes are in the range from about −2 to about −8 kV.

Electrophoretic separation of molecules on microfabricated devices and detection in situ of the separated analytes, typically by laser induced fluorescence has been described. However, the selectivity of fluorescence detection relaxes the requirement for sample purity compared to other, more general methods of detection. ESI-MS, being a general and sensitive detection method, limited the choice of materials which can be used for the construction of the system.

Figure 2B:
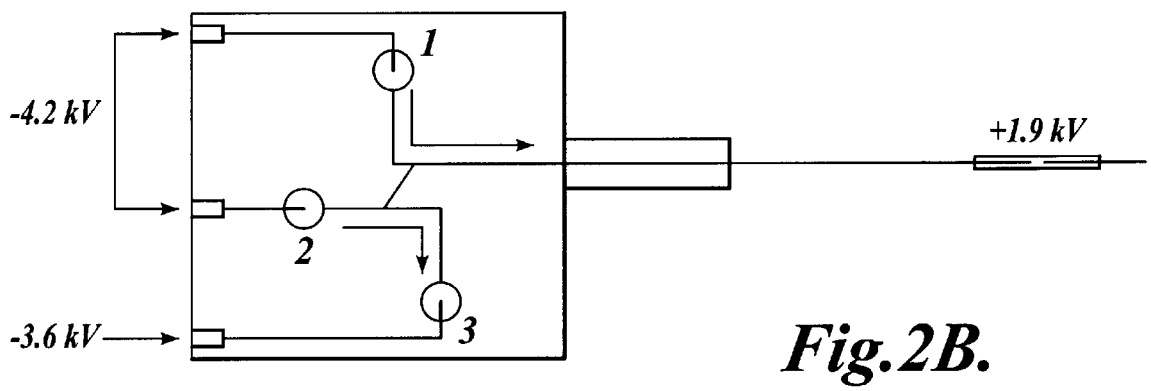
Figure 2C:
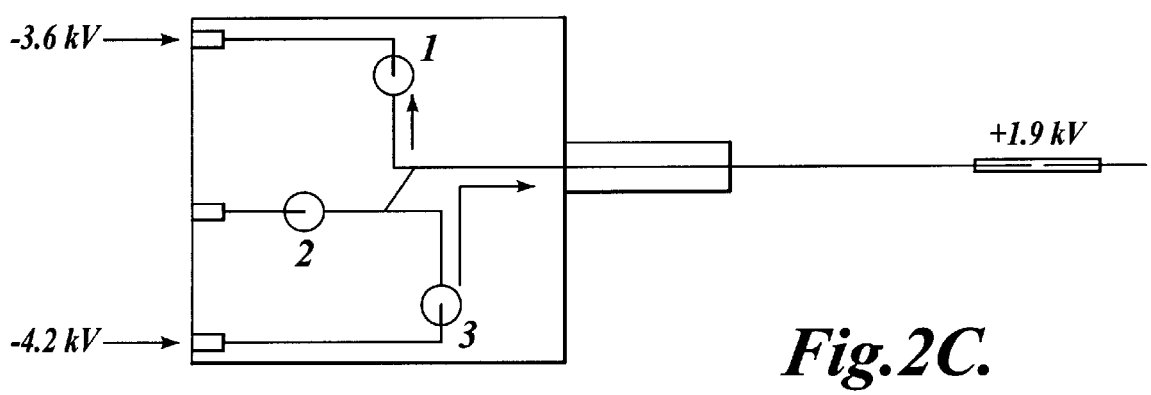
Figure 3:
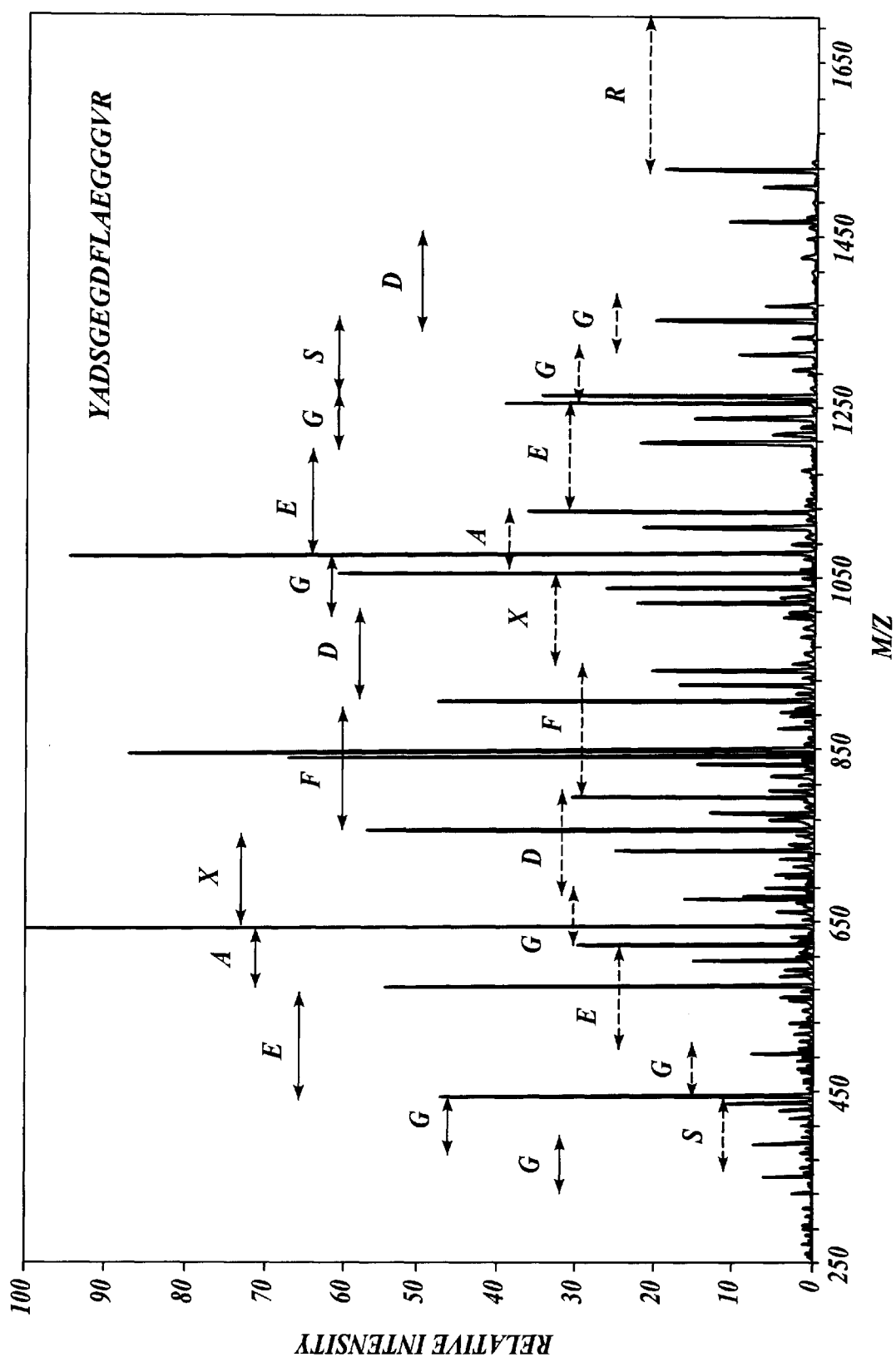
FIG. 3 is a tandem mass spectrum for fibrinopeptide A obtained by a representative system of the present invention.

By combining the fluidic device with an electrospray ionization mass spectrometer, the present invention provides a system for selectively and sequentially mobilizing and analyzing analytes such as peptide samples. To determine the sensitivity of detection achievable with the system of the present invention, solutions of decreasing concentration were analyzed using the configuration shown in FIG. 2A. Electroosmotic flow is indicated by the arrows on the device in FIGS. 2A–2C. Referring to FIG. 2A, a sample containing fibrinopeptide A was applied to reservoir 1 and electrophoresis buffer was introduced in reservoirs 2 and 3. The peptide was directed from reservoir 1 to the mass spectrometer by applying −5.0 kV at reservoir 1 and +1.7 kV at the microsprayer end of the pump while reservoirs 2 and 3 were left floating. The mass spectrometer was scanned in MS mode from 400 Da to 1000 Da. When the $(M+2H)^{2+}$ ion of fibrinopeptide A was detected at m/z=850.6, the instrument was switched manually to MS/MS mode and CID spectra were generated at different energies until sufficient information was generated. The average of the spectra was used to search a composite database containing 2,413 protein sequences using the Sequest program. Between each experiment, the device was thoroughly washed with acetonitrile, methanol, and buffer, respectively, until the signal for fibrinopeptide A fell below the detection level of the mass spectrometer. The experiments were repeated three times with independently prepared solutions. The tandem mass spectrum of fibrinopeptide A obtained at 33 fmol/µl (10 mM acetic acid pH 3.0 containing 10% (v/v) methanol) infused at an estimated flow rate of 200–300 nl/min is shown in FIG. 3. The Y ion series is indicated by a full line. The B ion series is indicated by a broken line. The letters in the right upper corner indicate the fibrinopeptide A amino acid sequence in the one letter code. To generate the spectrum shown in FIG. 3, two fmol of fibrinopeptide A was consumed. A Sequest search of the sequence database identified fibrinopeptide A with a correlation coefficient of 6.7 and a Δ correlation factor of 0.4. Both values are highly significant. The relevant spectra indicate that the limit of detection of the system operated in the MS mode was in the range of 2 fmol fibrinopeptide A/µl. The results obtained with capillary electrophoresis (i.e., CE-MS/MS) experiments on the same ion trap mass spectrometer showed that the sensitivity of detection for peptides in the MS/MS mode was better than the sensitivity of detection in the MS mode. The result is confirmed and illustrated in FIG. 3. Referring to FIG. 3, the signal-to-noise level in the CID spectrum is well above the limit of detection even though the signal of the peptide ion in the full scan mode (MS mode) approached the limit of detection. To further increase the sensitivity of detection of the present system, the dimensions of the channel, the capillary pump, and the microsprayer can be reduced.

Figure 4A:
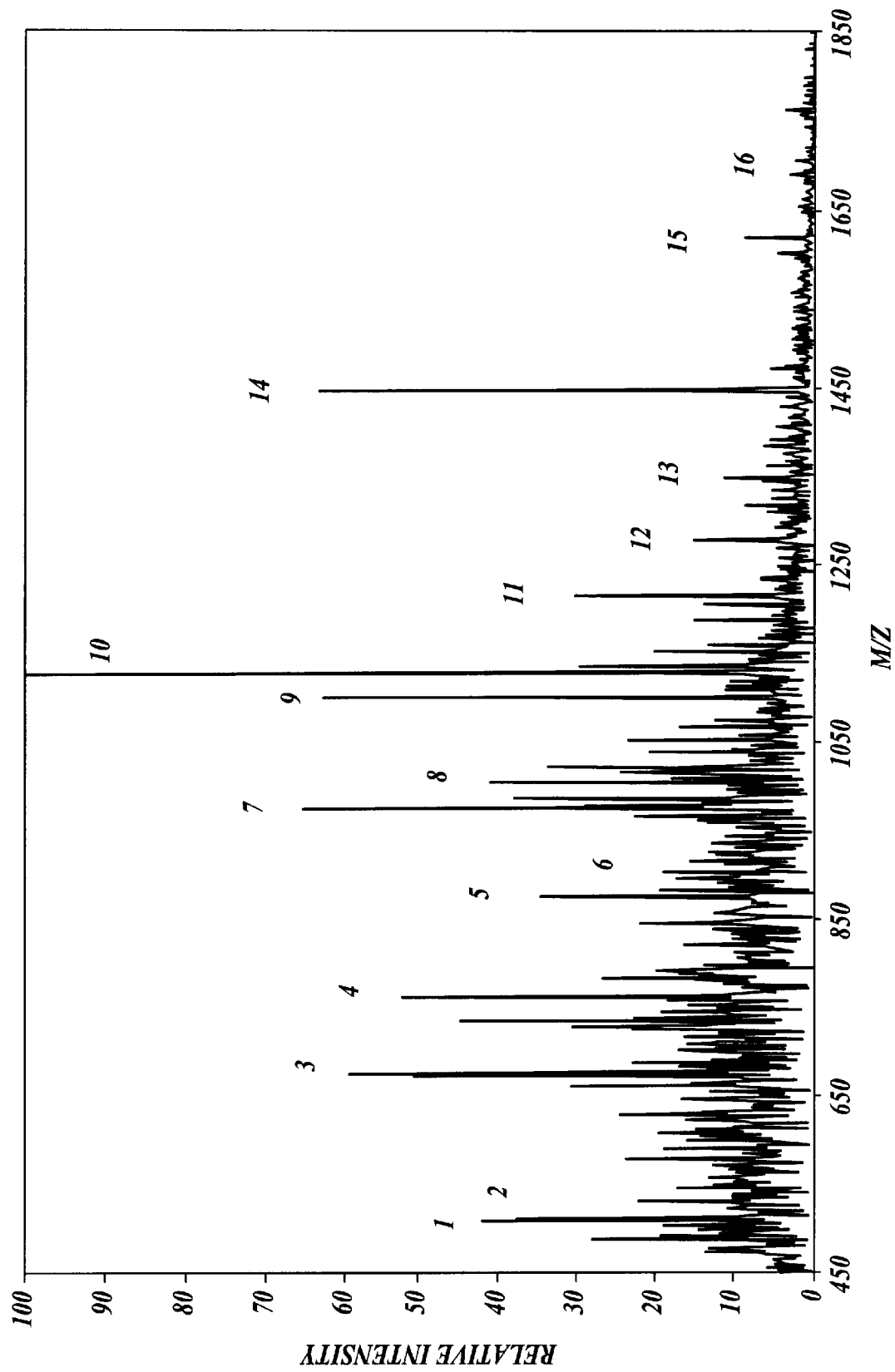
FIG. 4A is a mass spectrum for a tryptic digest of carbonic anhydrase (CA) by continuous infusion obtained by a representative system of the present invention.

The system of the present invention can be used for the identification of proteins based on the analysis of component peptides formed from enzymatic digestion. A tryptic digest of bovine carbonic anhydrase (CA) at a concentration of 290 fmol/µl (10 mM acetic acid pH 3.0 containing 10%(v/v) methanol) was introduced in reservoir 1. Reservoirs 2 and 3 contained electrophoresis buffer. Potentials of −4 kV and +1.85 kV were applied to reservoir 1 and the microsprayer, respectively, while reservoirs 2 and 3 were left floating (see FIG. 2A). The CA derived peptides were pumped from reservoir 1 toward the microsprayer and mass spectra were recorded in the ion trap mass spectrometer. Selected ions were subjected to CID and the generated fragment ion spectra were used to search a composite bovine sequence database using the Sequest software. A mass spectrum averaged over 19 scans, representing a total sample consumption of less than 30 fmol of CA tryptic digest is shown in FIG. 4A. Each peak was selected for CID and the resulting spectra were searched against a bovine database using the Sequest program. The peaks which contained peptides derived from CA are numbered and their respective identities are indicated in Table 1. The peptides which were identified as being derived from CA are numbered in FIG. 4A and the results of the respective Sequest database search are summarized in Table 1. In the table, correlation coefficient values greater than about 2.0 indicate a high level of confidence in the match.

TABLE 1

Bovine sequence database search with CID spectra of CA derived tryptic peptides.

| Peak | Mass ($MH^{+1}$) | Correlation coefficient | Δ correlation | Sequence | Position |
|---|---|---|---|---|---|
| 1 | 1012.5 | 3.7 | 0.45 | (K)VGDANPALQK (SEQ ID NO: 1) | 148–157 |
| 2 | 1018.5 | 2.5 | 0.21 | (K)DFPIANGER (SEQ ID NO: 2) | 18–26 |
| 3,13 | 1346.7 | 3.2 | 0.38 | (K)EPISVSSQQMLK (SEQ ID NO: 3) | 212–223 |
| 4 | 761.4 | 1.3 | 0.17 | (L)DALDSIK (SEQ ID NO: 4) | 160–166 |
| 5 | 874.5 | 1.6 | 0.15 | (V)LDALDSIK (SEQ ID NO: 5) | 159–166 |
| 6 | 913.5 | 1.4 | 0.26 | (V)GDANPALQK (SEQ ID NO: 6) | 149–157 |
| 7 | 973.5 | 2.4 | 0.24 | (K)VLDALDSIK (SEQ ID NO: 7) | 158–166 |
| 8 | 1002.6 | 1.8 | 0.11 | (D)GLAVVGVFLK (SEQ ID NO: 8) | 138–147 |
| 9 | 2198.2 | 4.4 | 0.58 | (K)AVVQDPALKPLALVYGEATSR (SEQ ID NO: 9) | 36–56 |
| 10 | 2253.2 | 5.6 | 0.45 | (K)YGDFGTAAQQPDGLAVVGVFLK (SEQ ID NO: 10) | 126–147 |
| 11 | 1214.7 | 3.0 | 0.51 | (Q)PDGLAVVGVFLK (SEQ ID NO: 11) | 136–147 |
| 12 | 1276.7 | 3.0 | 0.57 | (K)PLALVYGEATSR (SEQ ID NO: 12) | 45–56 |
| 14 | 1446.7 | 3.5 | 0.39 | (R)TLNFNAEGEPELL (SEQ ID NO: 13) | 226–238 |

TABLE 1-continued

Bovine sequence database search with CID spectra of CA derived tryptic peptides.

| Peak | Mass (MH$^{+1}$) | Correlation coefficient | Δ correlation | Sequence | Position |
|---|---|---|---|---|---|
| 15 | 1620.7 | 3.0 | 0.38 | (K)STDFPNFDPGSLLPN (SEQ ID NO: 14) | 171–185 |
| 16 | 1690.8 | 2.4 | 0.17 | (R)TLNFNAEGEPELLML (SEQ ID NO: 15) | 226–240 |

Figure 4B:
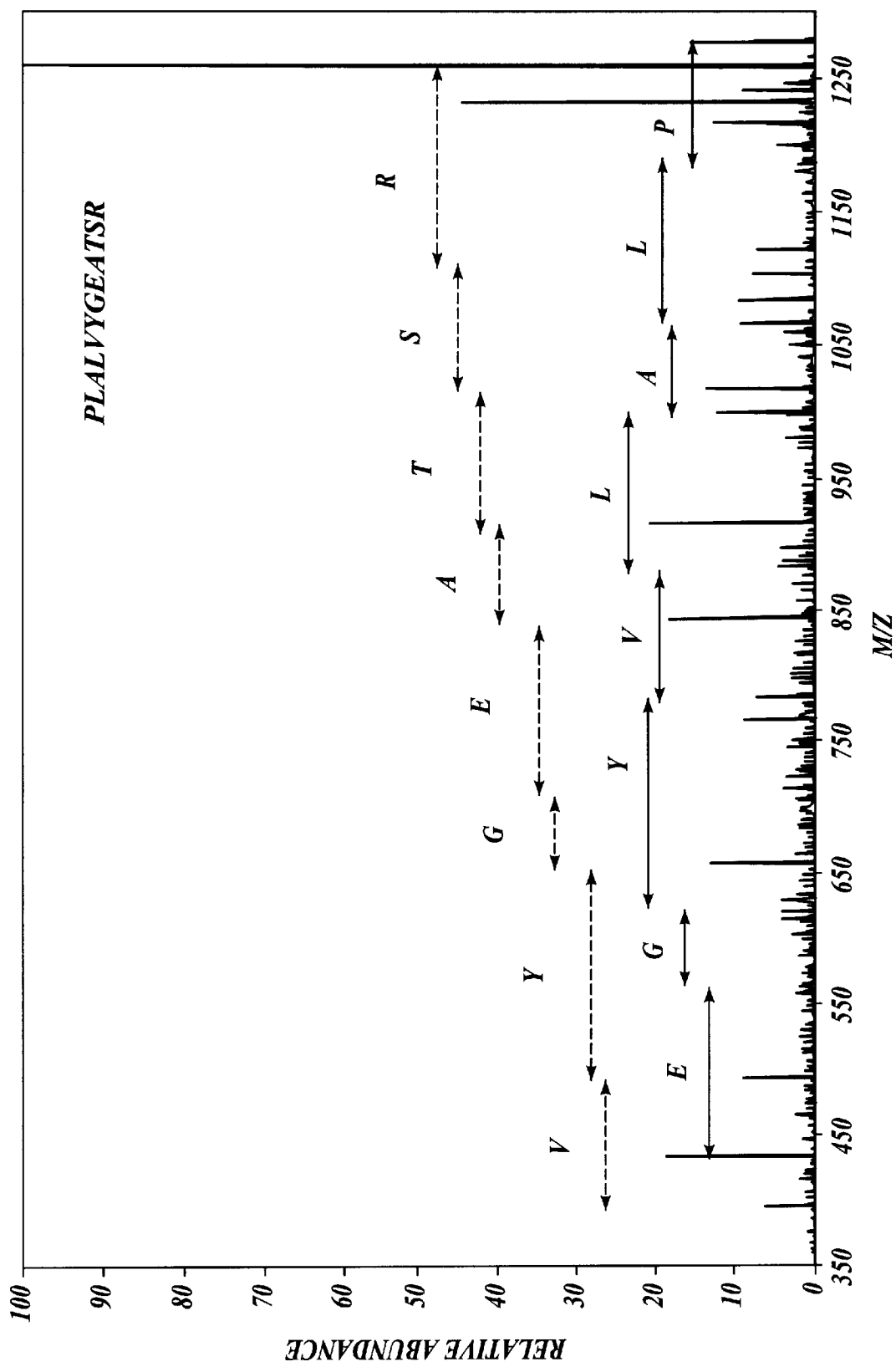
FIG. 4B is a tandem mass spectrum obtained for peak 12 from FIG. 4A.

Referring to FIG. 4A, a total of 15 peptides were identified as fragments of CA which individually and collectively provided unambiguous protein identification. As is typical for this type of analysis in which an unseparated peptide mixture is sprayed into the mass spectrometer, some of the peaks in the spectrum were not identified as being derived from CA. These peaks represented epoxy contaminants, solvent clusters, CID spectra of poor quality or contaminants of unknown origin and nature. As noted above, the sensitivity of the analysis was limited only by the ability to detect peptide ions in the MS mode. The limitation to detection is supported by the observation that even small peaks such as peaks identified as 12, 13, 15 or 16, whose intensities were below the noise level in some segments of the spectrum generated CID spectra, which identified the origin of the peptides with highly significant correlation coefficients. The CID spectrum for peak 12 is shown in FIG. 4B. The Y ion series is indicated by a full line. The B ion series is indicated by a broken line. The letters in the right upper corner indicate the amino acid sequence of the peptide in the one letter code. The quality of the spectrum is sufficient to read part of the sequence by interpreting the B and Y ion series.

In the system of the invention, samples can be concurrently applied to the device, sequentially mobilized and analyzed as described above. In the system, individual samples can be electrophoretically contained in their respective sample reservoirs, thus avoiding cross contamination. The configuration of the system for demonstrating the absence of cross-contamination in the system is shown in FIG. 2B. Tryptic digests of CA at a concentration of 290 fmol/μl and of BSA at a concentration of 130 fmol/μl were applied to reservoirs 1 and reservoir 3, respectively, while electrophoresis buffer was applied to reservoir 2. Tryptic digests of CA at 290 fmol/μl of BSA at 130 fmol/μl were sequentially infused from reservoirs 1 and 3, respectively, into the mass spectrometer using the configuration indicated in FIGS. 2B and 2C. Other parameters were as in FIG. 4 and the identities of the respective peptides are shown in Tables 2 and 3. Initially, the CA tryptic digest was mobilized toward the mass spectrometer by applying a potential of −4.2 kV at reservoir 1 and of +1.8 kV at the microsprayer. During the analysis of the CA sample, the BSA tryptic digest was contained in reservoir 3 by applying a potential of −4.2 kV to reservoir 2 and of −3.6 kV to reservoir 3 (see FIG. 2B). The potential difference between reservoirs 2 and 3 generated a slow flow of buffer towards reservoir 3, effectively isolating the analyte in reservoir 3. The analysis of the BSA tryptic digest followed. The BSA digest sample was pumped toward the MS by applying a potential of −4.2 kV at reservoir 3 and of +1.8 kV at the microsprayer (see FIG. 2C) while the remainder of the CA sample was contained in reservoir 1 by applying a potential of −3.6 kV to reservoir 1. Reservoir 2 was left floating. These conditions resulted in a small flow of BSA sample from reservoir 3 to reservoir 1, while most of the BSA flowed toward the mass spectrometer without cross contamination from the CA tryptic digest.

The mass spectrum obtained by the method described above for the CA tryptic digest is shown in FIG. 5A and the peaks identified as derived from CA by searching the bovine database with the MS/MS spectra are indicated in Table 2. In the table, correlation coefficient values greater than about 2.0 indicate a high level of confidence in the match.

TABLE 2

Bovine sequence database search with CID spectra of CA derived tryptic peptides.

| Peak | Mass (MH$^{+1}$) | Correlation coefficient | Δ correlation | Sequence | Position |
|---|---|---|---|---|---|
| 1,11 | 973.5 | 2.9 | 0.36 | (K)VLDALDSIK (SEQ ID NO: 7) | 158–166 |
| 2 | 1001.5 | 2.3 | 0.33 | (R)QSPVNIDTK (SEQ ID NO: 16) | 27–35 |
| 3 | 1012.5 | 3.5 | 0.43 | (K)VGDANPALQK (SEQ ID NO: 1) | 148–157 |
| 4,12 | 1018.5 | 1.8 | 0.12 | (K)DFPIANGER (SEQ ID NO: 2) | 18–26 |
| 5 | 1066.5 | 2.9 | 0.47 | (L)ALVYGEATSR (SEQ ID NO: 17) | 47–56 |
| 6,15 | 1150.7 | 2.9 | 0.42 | (K)AVVQDPALKPL (SEQ ID NO: 18) | 36–47 |
| 7,18 | 1346.7 | 3.4 | 0.46 | (K)EPISVSSQQMLK (SEQ ID NO: 3) | 212–223 |
| 8 | 2098.9 | 4.8 | 0.36 | (R)MVNNGHSFNVEYDDSQDK (SEQ ID NO: 19) | 58–75 |
| 9 | 874.5 | 1.4 | 0.29 | (V)LDALDSIK (SEQ ID NO: 5) | 159–166 |

TABLE 2-continued

Bovine sequence database search with CID spectra of CA derived tryptic peptides.

| Peak | Mass (MH$^{+1}$) | Correlation coefficient | Δ correlation | Sequence | Position |
|---|---|---|---|---|---|
| 10 | 913.5 | 1.4 | 0.26 | (V)GDANPALQK (SEQ ID NO: 6) | 149–157 |
| 13 | 2198.2 | 4.7 | 0.53 | (K)AVVQDPALKPLALVYGEATSR (SEQ ID NO: 9) | 36–56 |
| 14 | 2253.2 | 5.2 | 0.53 | (K)YGDFGTAAQQPDGLAVVGVFLK (SEQ ID NO: 10) | 126–147 |
| 16 | 1214.7 | 3.2 | 0.55 | (Q)PDGLAVVGVFLK (SEQ ID NO: 11) | 136–147 |
| 17 | 1276.7 | 2.8 | 0.55 | (K)PLALVYGEATSR (SEQ ID NO: 12) | 45–56 |
| 19 | 1446.7 | 2.2 | 0.06 | (R)TLNFNAEGEPELL (SEQ ID NO: 13) | 226–238 |
| 20 | 1620.7 | 2.0 | 0.30 | (K)STDFPNFDPGSLLPN (SEQ ID NO: 14) | 171–185 |

Figure 5A:
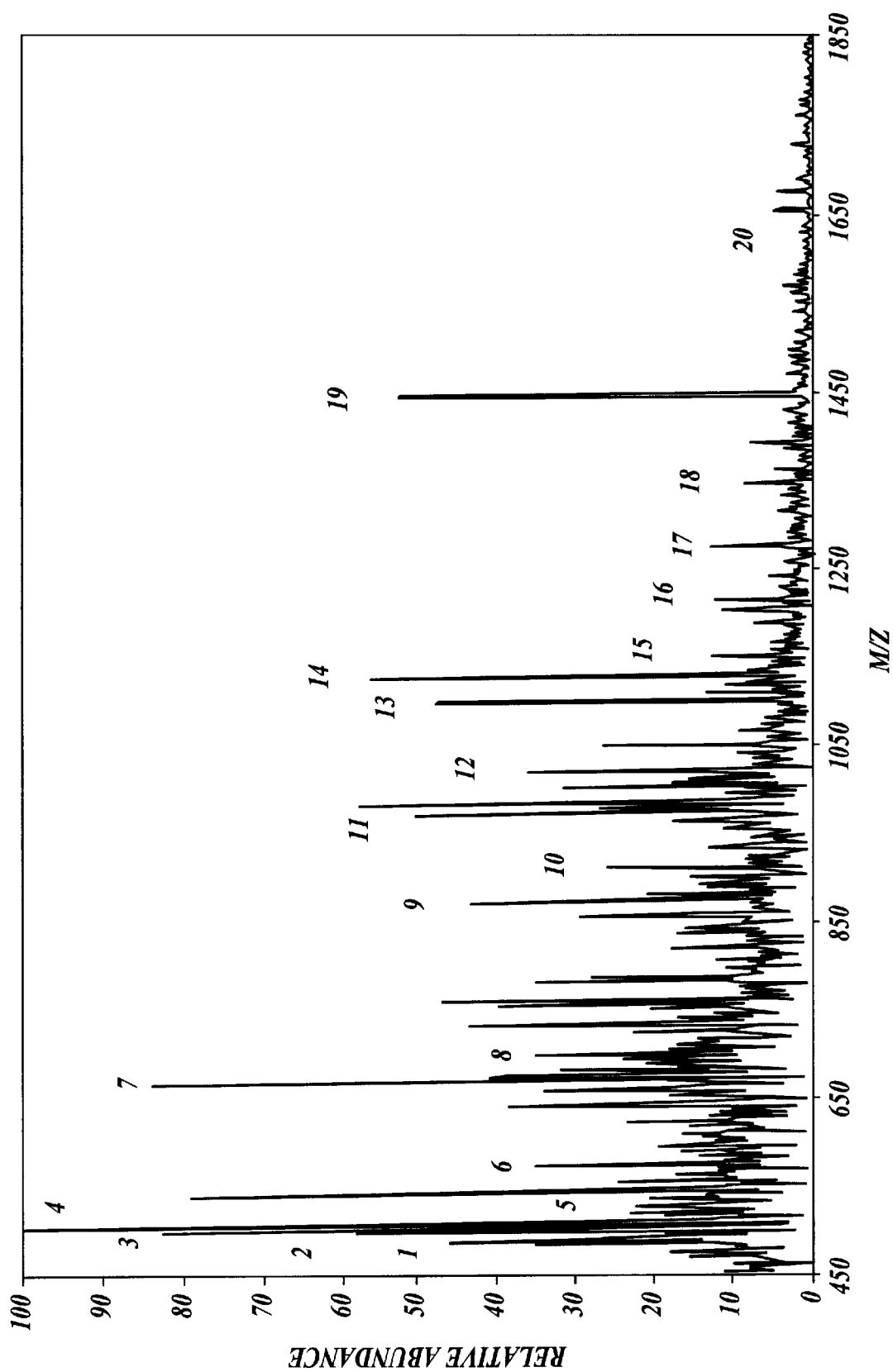
FIGS. 5A and 5B are mass spectra for tryptic digests of CA and bovine serum albumin (BSA), respectively, in sequential sample mobilization mode obtained by a representative system of the present invention.

The unlabeled peaks in FIG. 5A were either from epoxy, other contaminants, solvent clusters or CID spectra of poor quality. The multiplexed mode achieved unambiguous identification of CA. The MS spectrum obtained was substantially the same as the one obtained for the same sample in the single sample mode (see FIG. 4A). Furthermore, in the method, no peptides from the BSA sample were detected.

Figure 5B:
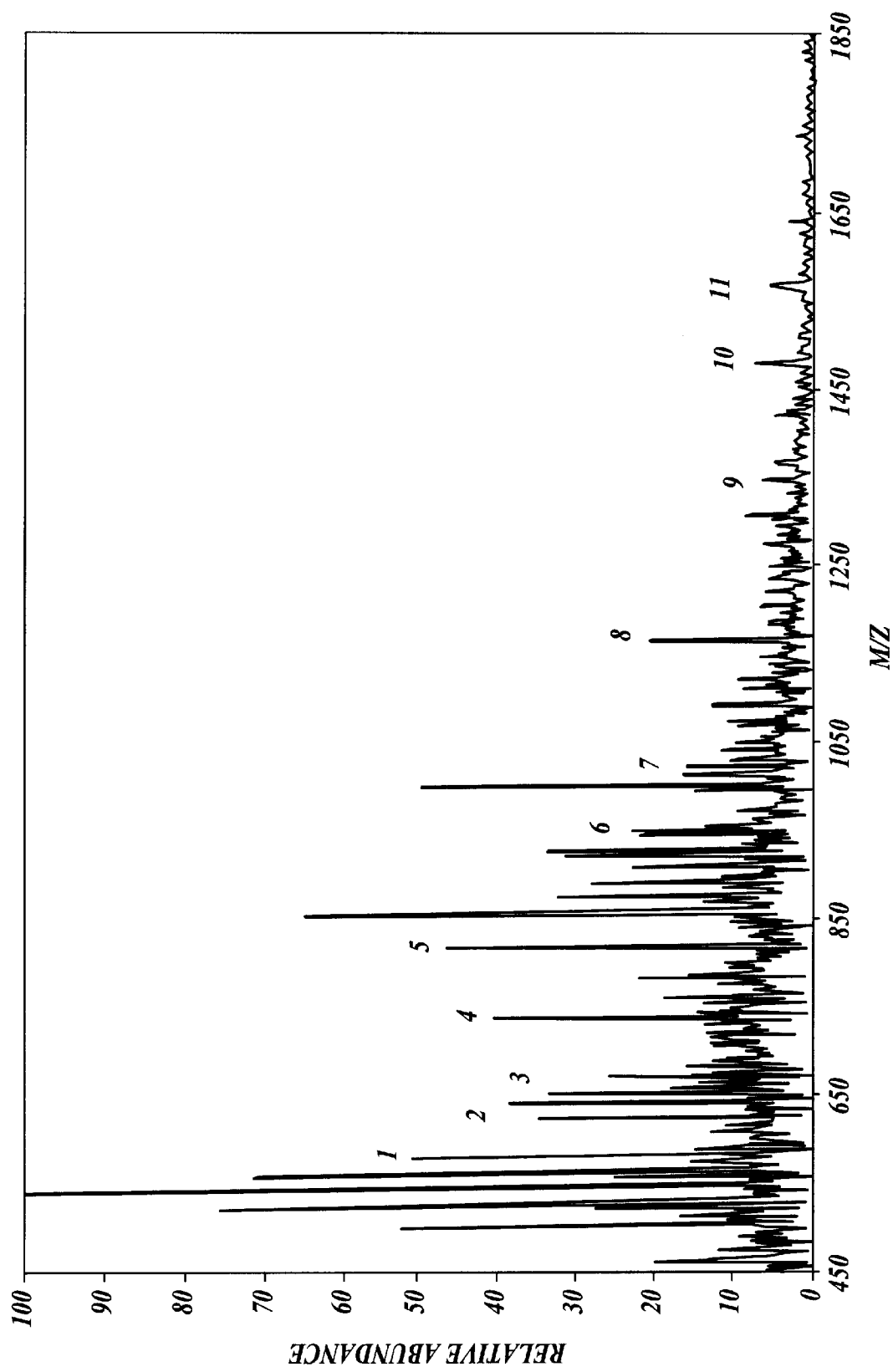

An average mass spectrum obtained from the BSA sample by the method is shown in FIG. 5B and the Sequest database search results are summarized in Table 3. In the table, correlation coefficient values greater than about 2.0 indicate a high level of confidence in the match.

TABLE 3

Bovine sequence database search with CID spectra of BSA derived tryptic peptides

| Peak | Mass (MH$^{+1}$) | Correlation coefficient | Δ correlation | Sequence | Position |
|---|---|---|---|---|---|
| 1,8 | 1163.6 | 2.1 | 0.14 | (K)LVNELTEFAK (SEQ ID NO: 20) | 42–51 |
| 2 | 1249.6 | 1.4 | 0.16 | (R)FKDLGEEHFK (SEQ ID NO: 21) | 11–20 |
| 3,9 | 1305.7 | 3.4 | 0.48 | (K)HLVDEPQNLIK (SEQ ID NO: 22) | 378–388 |
| 4,10 | 1479.8 | 4.2 | 0.57 | (K)LGEYGFQNALIVR (SEQ ID NO: 23) | 397–409 |
| 5 | 1639.9 | 3.2 | 0.46 | (R)KVPQVSTPTLVEVSR (SEQ ID NO: 24) | 414–428 |
| 6 | 1888.9 | 2.8 | 0.43 | (R)HPYFYAPELLYYANK (SEQ ID NO: 25) | 145–159 |
| 7 | 2045.0 | 3.2 | 0.46 | (R)RHPYFYAPELLYYANK (SEQ ID NO: 26) | 144–159 |
| 11 | 1567.7 | 2.2 | 0.22 | (K)DAFLGSFLYEYSR (SEQ ID NO: 27) | 363–375 |

The numbered peaks were identified as being derived from BSA. Again, the peaks which were not identified after CID analysis were either from epoxy, other contaminants, solvent clusters or spectra of poor quality. BSA was unambiguously identified as being the protein present in this sample and no CA peptides were detected.

These results indicate that different samples can be concurrently present on the device, sequentially mobilized without cross contamination, and analyzed. Switching from one analyte to the next is simply achieved by changing the potentials applied to the individual reservoir. In the method, the tedious step of realigning the microsprayer for each sample is eliminated. Indeed, a significant advantage of the device and method of the invention is the possibility of delivering a standard sample from one reservoir until the sprayer is optimally positioned and the MS parameters optimized, prior to the unknown analyte being introduced into the MS and analyzed.

To summarize, in one aspect, the present invention provides a device that can be combined with an ESI mass spectrometer to provide a system for the identification of peptide analytes. The analytes are delivered from the device to the mass spectrometer by means of an electroosmotic pump positioned between the device and the microspray ion source. The dimensions of the pump and the potential differential over the system can control the flow rate. The system can be utilized to identify proteins by the CID spectra of selected peptides in protein tryptic digests at the fmol/μl level. The device and method of the present invention provides for the sequential interrogation by the mass spectra of analytes which are concurrently present on the device, without detectable cross contamination between samples.

In another aspect, the present invention provides an integrated analytical system that includes a fluidics device, preferably micromachined using photolithography/etching technology; a panel of computer-controlled high voltage relays; and an electrospray ionization tandem mass spectrometer. Movement of solvents and samples on the device and from the device to the mass spectrometer is achieved by directed electroosmotic pumping induced by the activation of a suitable constellation of high voltage relays. The system can be used for the sequential automated analysis of protein digests. The system achieves low fmol/µl sensitivity of detection and is compatible with the analysis of proteins separated by two-dimensional gel electrophoresis.

The system of the invention is useful in the automated identification of proteins separated by high resolution two-dimensional gel electrophoresis (2DE). The system achieves concentration limits of detection (LOD) in the low fmol/µl range and sequential, automated analysis of samples concurrently present on the fluidic device. The system and method of the invention are adaptable to many analytical problems beyond protein analysis that require fast, unambiguous, automated and sensitive analysis of complex mixtures of analytes.

Figure 6:
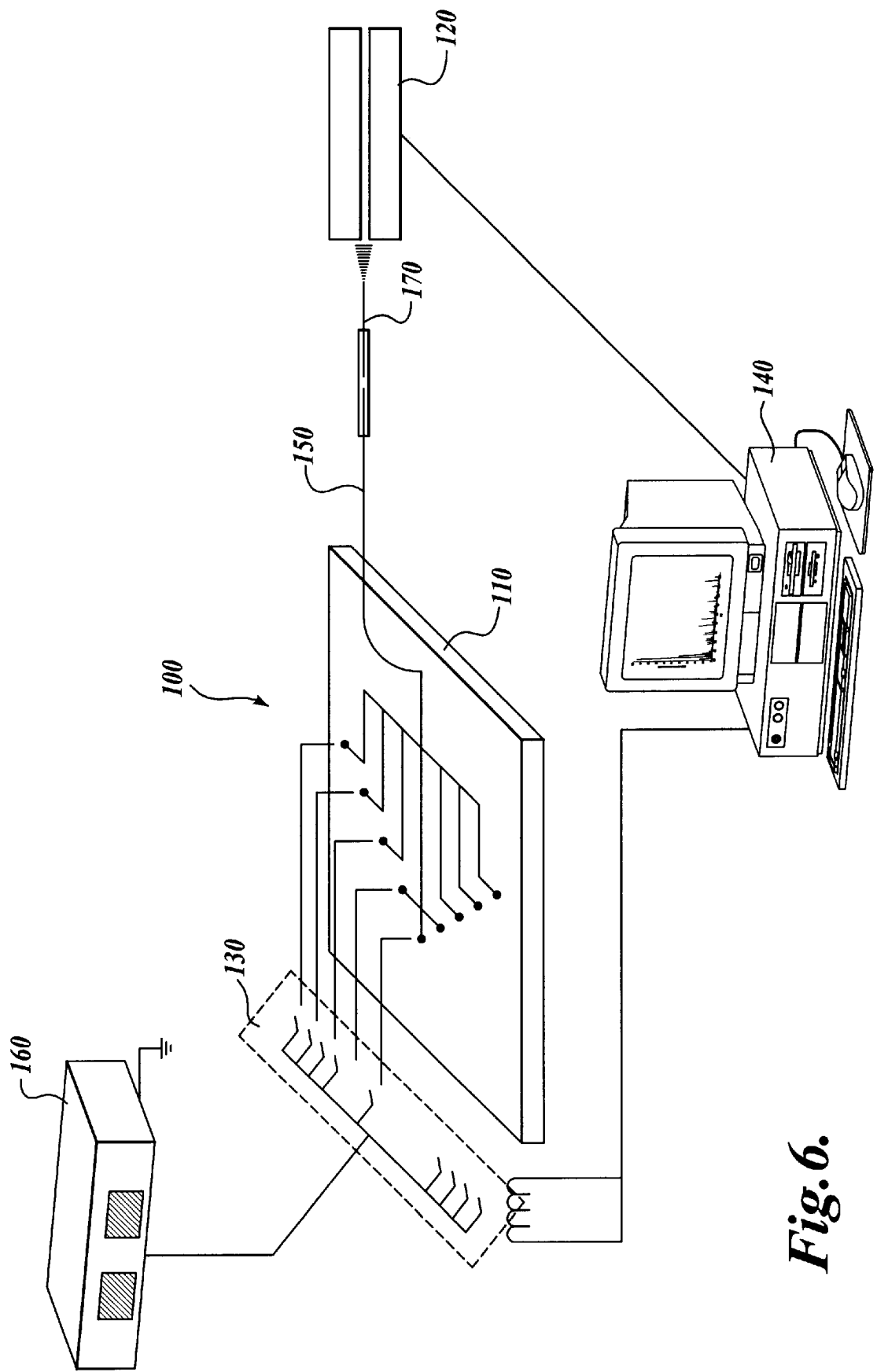
FIG. 6 is a schematic diagram of a representative system of the present invention including a nine-position fluidics device coupled to a mass spectrometer by a transfer capillary and microelectrospray ionization source and a computer-controlled high voltage relay array.

A representative system of the present invention is schematically illustrated in FIG. 6. Referring to FIG. 6, system 100 includes device 110 for sequential sample delivery; mass spectrometer 120 for the structural analysis of analytes; an array 130 of high voltage relays controlling direction, origin, and magnitude of the electroosmotic flow of the analyte solutions; and a computer workstation 140 for controlling the relays and the mass spectrometer, and for analyzing the generated data.

In the illustrated system, device 110 includes nine reservoirs (i.e., 111–119) connected via channels (i.e., 121–129) to transfer capillary 150. Reservoirs and channels are etched in glass using a photolithographic mask and an isotropic etching process with hydrofluoric acid. The samples are applied to the reservoirs and one sample at a time is mobilized by inducing an electroosmotic flow from the specific reservoir through the transfer capillary to the mass spectrometer. The flow is controlled by high voltage electrodes (e.g., 131–139) which are connected by computer-controlled relay 130 to high voltage power supply 160. The electrospray ionization source 170 at the end of transfer capillary 150 interfaces the sample delivery module with the mass spectrometer (e.g., MS/MS) in which selected peptide ions were subjected to collision-induced dissociation. The resulting CID spectra are recorded and then searched against a protein or DNA database using the Sequest software. The cycle can be automatically repeated by mobilizing the sample in the next reservoir until all samples initially applied to the device are analyzed.

The device illustrated in FIG. 6 was made from a piece of glass (540 µm thick) generally as described above for device 10. The device was connected to a micro ESI source via a 15 cm long of fused silica transfer capillary (75 µm i.d.×150 µm o.d.) which was derivatized on the inner surface with 3-aminopropylsilane. The link between the device and the capillary was made by inserting a 200 µm i.d.×350 µm o.d. sheath capillary into the 350 µm hole at the end of the main channel (i.e., the fluid exit) and gluing it in place using heat-curable epoxy. A 250 µm i.d. and 1.5 mm o.d. TEFLON tube was inserted over the sheath capillary and glued in place. A small section of the TEFLON tube had been previously expanded to fit the full length of the sheath capillary. A fingertight fitting was added to the end of the TEFLON tubing. A transfer capillary was inserted into the TEFLON tube and into the sheath capillary so that its end reached into the etched channel on the device. The transfer capillary was held in place by tightening the fingertight fitting. The whole transfer assembly was sealed and stabilized by a "dual shrink" TEFLON tube placed over the sheath capillary. The liquid junction microESI ion source was as described (Figeys, D., Ducret, A., Yates, J. R. III and Aebersold, R., *Nature Biotech.*, 14:1579–1583 (1996); Figeys, D., Ducret, A. and Aebersold, R., *J. Chromatogr. A*, 763:295–306 (1997)). The spraying potential applied to the ion source was supplied by the power supply of the ITMS and was held constant at +1.3 to +1.7 kV for the duration of an experiment.

The electronic circuit which controlled the voltage applied to each reservoir consisted of nine high voltage relays (Kilovac, CA) under the control of optorelays. These were connected to a digital analog converter board (National Instruments, TX) and activated by a program written in Labview (National Instruments). The Labview program was triggered through the LCQ software using the driving voltage of the divert valve. This voltage was applied to a 2.4 kΩ resistor in series with an optorelay to ground. The optorelay connected +5V to a digital input/output from the DAQ board. All the electronic and computer control procedures are transparent to the user. The only interventions required are setting of the proper parameters on the LCQ software for automated data acquisition and generation of CID spectra.

At the beginning of an analysis all the reservoirs, channels and capillaries were filled with electrophoresis buffer (10 mM acetic acid:methanol 10% (v/v) pH 3.0). The buffer was electroosmotically pumped towards the mass spectrometer and the micro ESI source was aligned with the entrance of the MS using an XYZ translation stage. Once an optimal sprayer position was achieved, electrophoresis buffer in the reservoirs was replaced with sample solutions. The samples were mobilized from the reservoir by applying −5 kV to the respective reservoir and +1.3 to +1.7 kV to the micro ESI ion source. Each reservoir was connected to a specific high voltage relay and the potential at each reservoir was controlled by the Labview program.

The ITMS was used essentially as described (Figeys, D. and Aebersold, R., *Electrophoresis*, 18:360–368 (1997)) except that the selection of peptide ions for CID was automated and that the computer controlling the ITMS also controlled the high voltage relay system. In MS mode the target number of ions was set to $9 \times 10^7$ and in CID mode to $1 \times 10^7$. In a typical experiment the ITMS triggered the Labview procedure which in turn applied the voltage to the appropriate reservoir. The first 14.3 minutes of acquisition were done in MS mode only, scanning the range from 500 to 1400 Da. This left sufficient time for the analyte mixture to reach the MS. The ITMS then automatically acquired MS and MS/MS data in three segments of the spectrum. Peptide ions in the first segment (510 to 710 Da) were fragmented at 35% of collision energy. Ions in the second segment (710 to 920 Da) were fragmented at 45% collision energy and ions in the third segment (920 to 1120 Da) were fragmented at 50% of collision energy. The segments were subdivided into sections of 10 Da and the ion with the highest intensity was automatically detected and selected for CID using a 3 Da window centered around the mass of the selected ion. Each 10 Da window required a cycle time of 0.26 min. Since the program for the analysis of each section constituted a complete method file, the high voltage was automatically turned off while the method for the analysis of the next segment was loaded in the computer. The CID spectra generated were recorded and used to determine the identity of the protein from which the peptide originated.

Figure 7A:
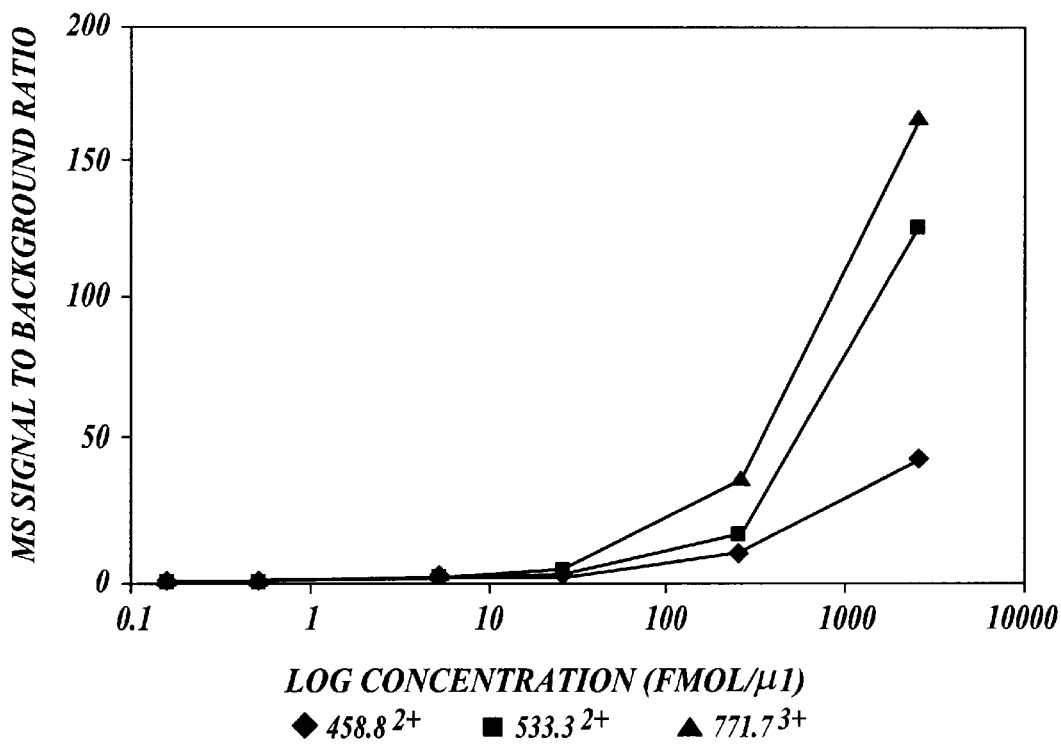
FIGS. 7A and 7B are graphs illustrating the sensitivity of detection measurement with a representative system of the present invention.
Figure 7B:
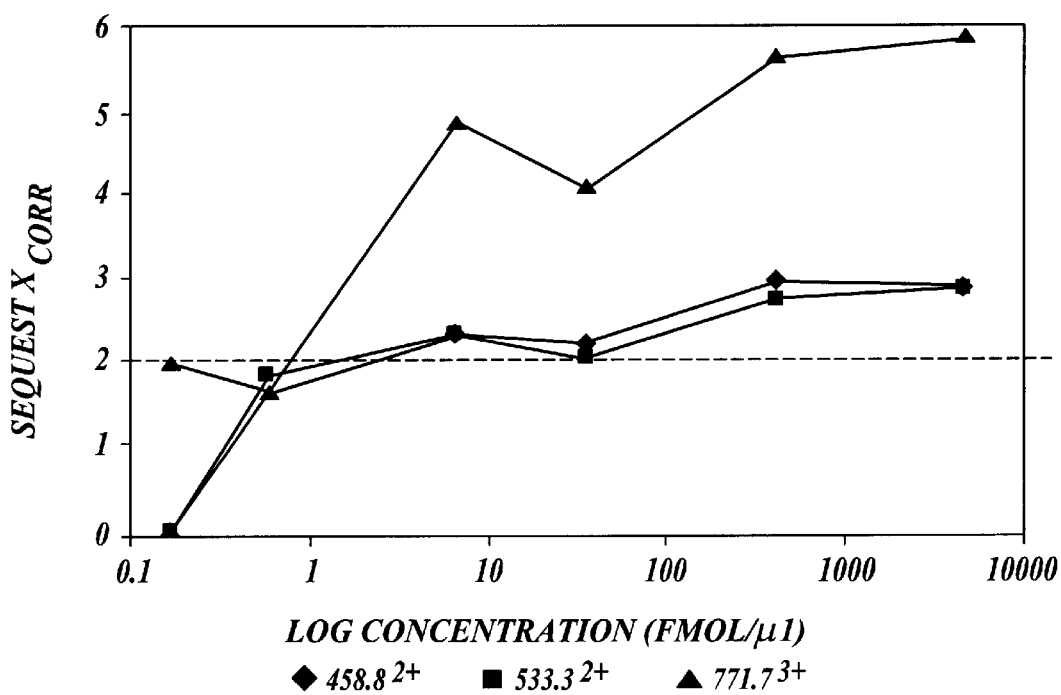

The concentration LOD attainable with the representative system illustrated in FIG. 6 was determined by applying tryptic digests of β-lactoglobulin (βlac) calibrated to concentrations between 160 amol/μl and 2.6 pmol/μl to reservoir 2 and analyzing the sensitivity of detection by monitoring selected peptides by ESI-MS and ESI-MS/MS. The results shown in FIG. 7A indicate that peptides exceeding a concentration of 5 fmol/μl are detectable in MS mode. The cross correlation factor (Xcorr), which was calculated by the Sequest software when the generated CID spectra were searched against a bovine protein database, was used to determine the LOD in MS/MS mode. The factor indicates the quality of the correlation and a value of 2 empirically considered significant. The results shown in FIG. 7B indicate that Xcorr values exceeding two were achieved at sample concentrations between 160 amol/μl (m/z=771.7) and 1 fmol/μl (m/z=458.8; m/z=533.3). The higher LOD achieved in MS/MS compared to the MS mode is a consequence of the ability of the ITMS instrument to accumulate ions of a specific m/z ratio prior to CID.

Using the system of the invention, the identification of βlac was conclusive at subfmol/μl concentration. Such a sensitivity is comparable to the sensitivity achieved by nanoESI-MS and sample delivery through fused silica capillaries. The sensitivity achieved by the system can be further improved by reducing the size of the etched channels and by reducing the chemical noise through the introduction of clean gas at the microESI interface.

Automated, sequential analysis of samples deposited concurrently on the fluidic device is optimal when sample-to-sample cross contamination is minimized. The lack of cross contamination in the system of the invention is demonstrated by applying tryptic digests of βlac, carbonic anhydrase (CA), and bovine serum albumin (BSA) to adjacent reservoirs one to three, respectively, and sequentially mobilized by manually switching the high voltage relays. To make even minor sample-to-sample cross contaminnation detectable, these analyses were done at concentrations of approximately 200 fmol/μl, which exceed the LOD by a factor of at least 50. One sample at a time was mobilized towards the mass spectrometer and CID spectra at every m/z value were manually generated in the range between 450 and 1800 Da. Data acquisition was started 14 min. after mobilization of a new sample to allow for the new sample to replace the previous one in the shared segments of the flow path. Analysis of the resulting CID spectra indicated that, in the case of βlac, sample 13 peptides were identified as derived from βlac. No peptide from either BSA or CA was detected. For the CA sample, five CA-derived peptides were identified and one βlac peptide and no BSA peptide were detected. In the BSA sample, 12 BSA peptides were identified and no BSA or βlac peptides were detected. In 17 experiments of this type, an average of 0.7±0.7 contaminant peptides were observed. Furthermore, contaminating peptides were observed to be present in low amounts. These results indicate that samples concurrently present on the device could be sequentially analyzed with minimal sample-to-sample cross contamination. In cases in which a higher number of cross-containations was observed, the liquid flow on the device was found to be impeded by partial blocking of a channel. The number of cross-contarminating peptides, while already low, can further be reduced either by flushing the common segments of the flow path with electrophoresis buffer present in one of the reservoirs, by moving the samples back into their respective reservoirs after analysis, or by chemically derivatizing the wetted surfaces to minimize non-specific peptide absorption.

The manual sample mobilization and analysis procedure can be automated by implementing a computer program that coordinately controls the sample flow from the appropriate reservoir to the ion trap mass spectrometer and the generation and analysis of CID spectra of selected ions. Human intervention can be limited to inserting samples into the reservoirs and starting the analysis.

Figure 8A:
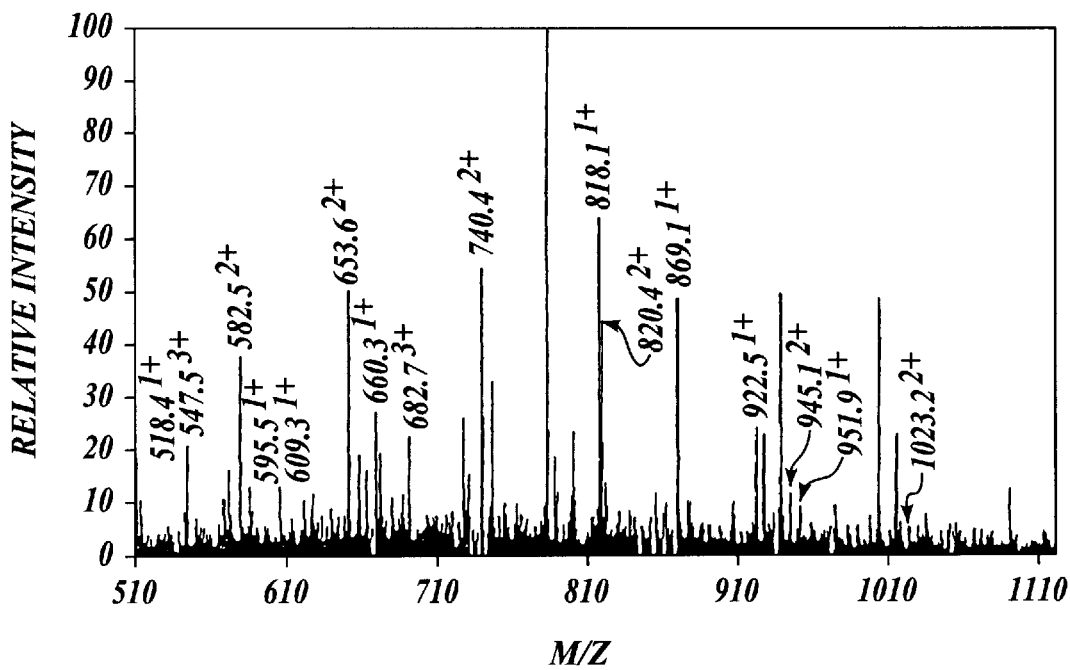
FIGS. 8A–8C are mass spectra obtained from a representative system of the present invention with automated analysis of calibrated samples.
Figure 8B:
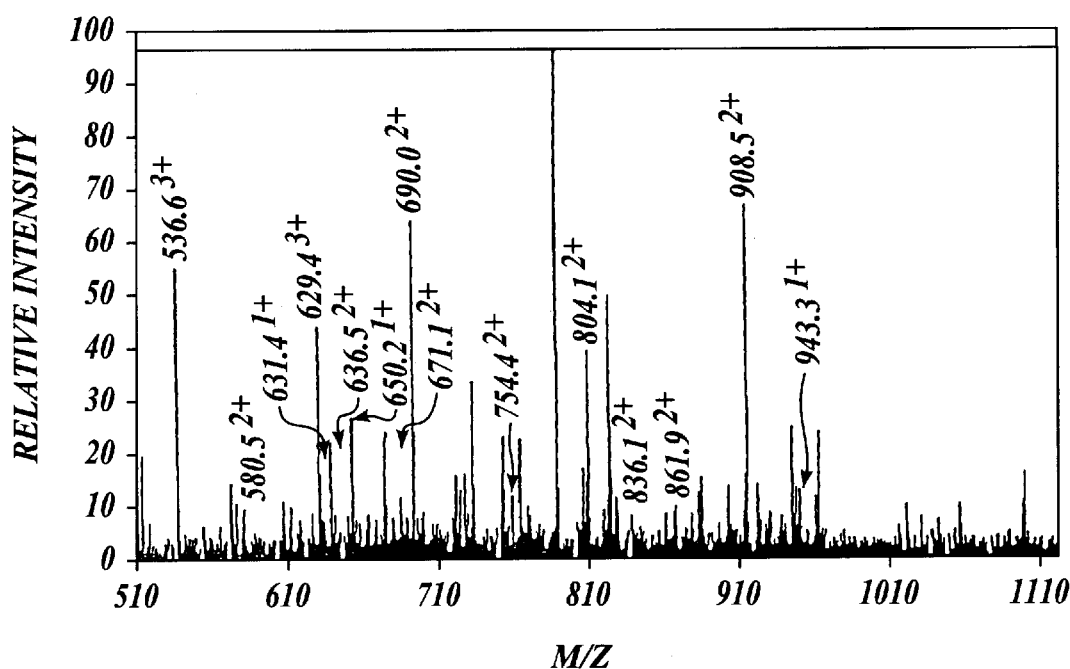
Figure 8C:
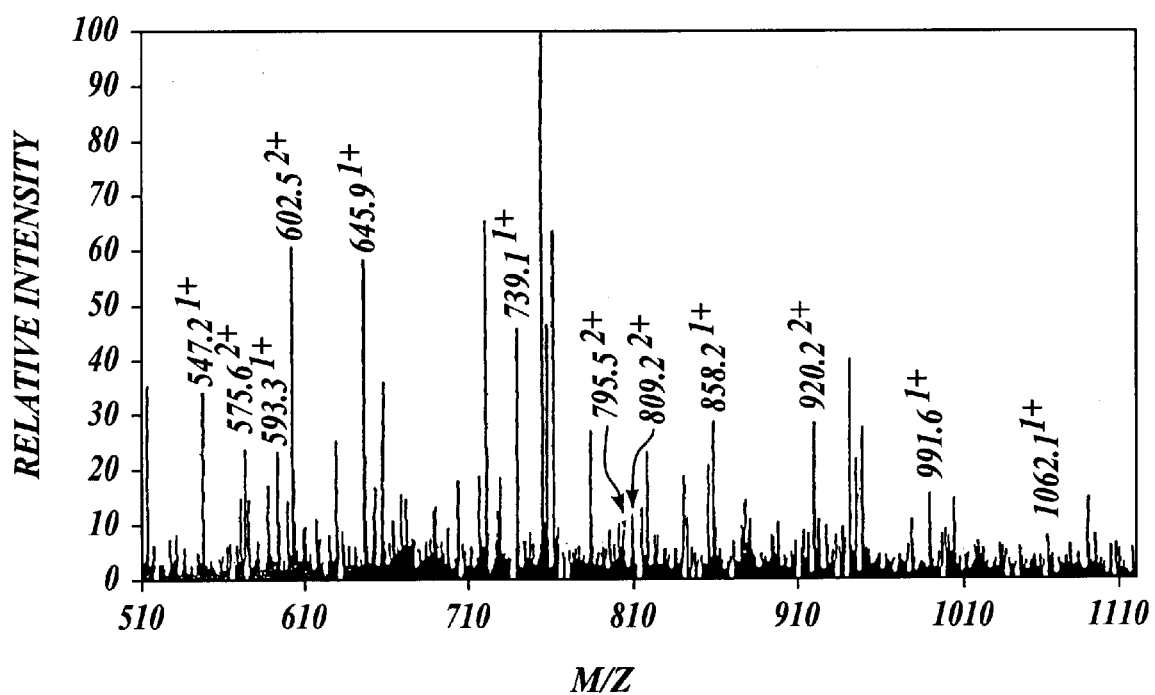

Results from the automated analysis of calibrated protein samples by a representative system of the invention are shown in FIGS. 8A–8C. Referring to FIG. 6, tryptic digests of BSA, horse myoglobin (Mb), and human haptoglobin 2-1 (Hg) were applied to reservoirs one to three and five to seven, respectively. Reservoirs four, eight, and nine were filled with electrophoresis buffer. The samples were automatically sequentially mobilized and analyzed. The number of peptides identified varied from 12 to 18 for the proteins tested and unambiguously identified the respective proteins. FIGS. 8A–8C illustrate the mass spectra obtained by the system for BSA tryptic digest flowing from reservoir 1 at 182 fmol/μl, Mb tryptic digest from reservoir 2 at 237 fmol/μl, and Hg tryptic digest from reservoir 3 at 222 fmol/μl. Results from the analysis of the samples present in reservoirs one to three (FIGS. 8A–8C) were indistinguishable from the results obtained from the same samples placed in reservoirs five to seven and analyzed in the same experiment (data not shown). Furthermore, as with the manual procedure, sample-to-sample cross contamination with the automated procedure was minimal.

Figure 9:
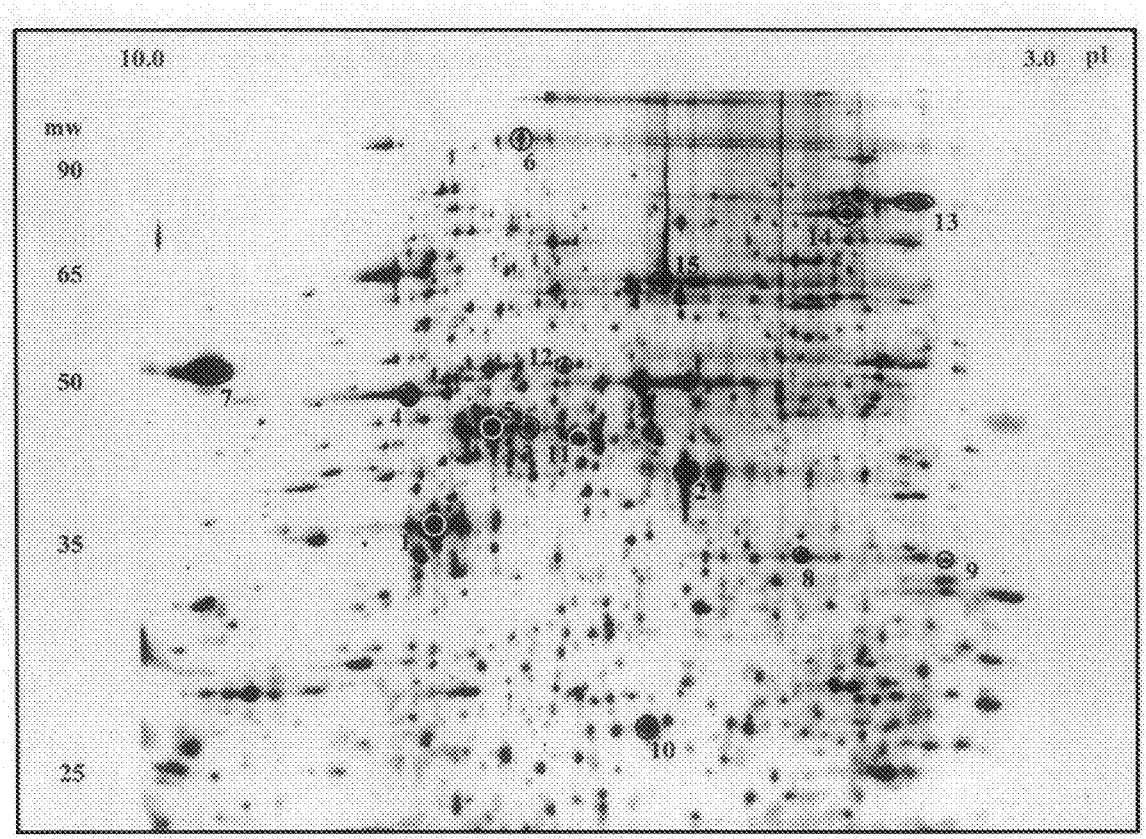
FIG. 9 is a 2D gel electropherogram of yeast proteins: aliquots of total yeast (S. Cerevisea) lysate containing 40 μg of protein were separated by 2D electrophoresis (isoelectric focusing/SDS polyacrylamide gel electrophoresis) and detected by silver staining; Spot 1 was identified as G3P1, with a calculated pI of 8.3 and a molecular weight of 35618; Spot 2: ALF, 5.5, 39490; Spot 3, ADH1, 6.3, 36692; Spot 4, PGK, 7.1, 44607; Spot 5, ADH1, 6.3, 36692; Spot 6, METE, 6.1, 85728; Spot 7, EF1A, 9.1, 50032; Spot 8, IPYR, 5.4, 32184; Spot 9, GBLP, 5.8, 34805; Spot 10, TPIS, 5.7, 26664; Spot 11, MPG1, 6.0, 39566; Spot 12, MT17, 6.0, 48540; Spot 13, HS72, 4.9, 69338; Spot 14, HS75, 5.3, 66470; and Spot 15, DCP1, 6.0, 61468.

To evaluate the performance of the automated system at higher sensitivity and under realistic experimental conditions, proteins separated by 2DE were analyzed. A representative 2D gel electropherogram is shown in FIG. 9.

2D gel electrophoresis of total lysate of yeast strain S288C was performed exactly as described (Figeys, D., Ducret, A., Yates, J. R. III and Aebersold, R., Nature Biotech. 14:1579–1583 (1996); Garrels, J. I., Futcher, B., Kobayashi, R., Latter, G., Schwender, B., Volpe, T., et al., Electrophoresis, 15:1466–1486 (1994)), except that 40 μg of total protein per gel was applied. Proteins were visualized by a silver-stain method modified from Blum et al. (Blum, H., Beier, H. and Gross, H. J., Electrophoresis 8:93–99 (1987)). Proteins were excised from the gel and digested with trypsin (Shevchenko, A., Wilm, M., Vorm, O. and Mann, M., Anal. Chem., 68:850–858 (1996)). Each digest was pressure loaded on a small C18 bed inserted in a gel loading tip. The beads were rinsed with 10 mM acetic acid:methanol 10% (v/v) and the peptides were eluted using 65% acetonitrile. Dried samples were resuspended in 15 μl of 10 mM acetic acid:methanol 10% (v/v). Using an identical $^{35}$S-methionine labeled gel, protein levels in spots were estimated by amino acid analysis of intense spots and scintillation counting to give an average specific activity normalized per methionine.

Figure 10:
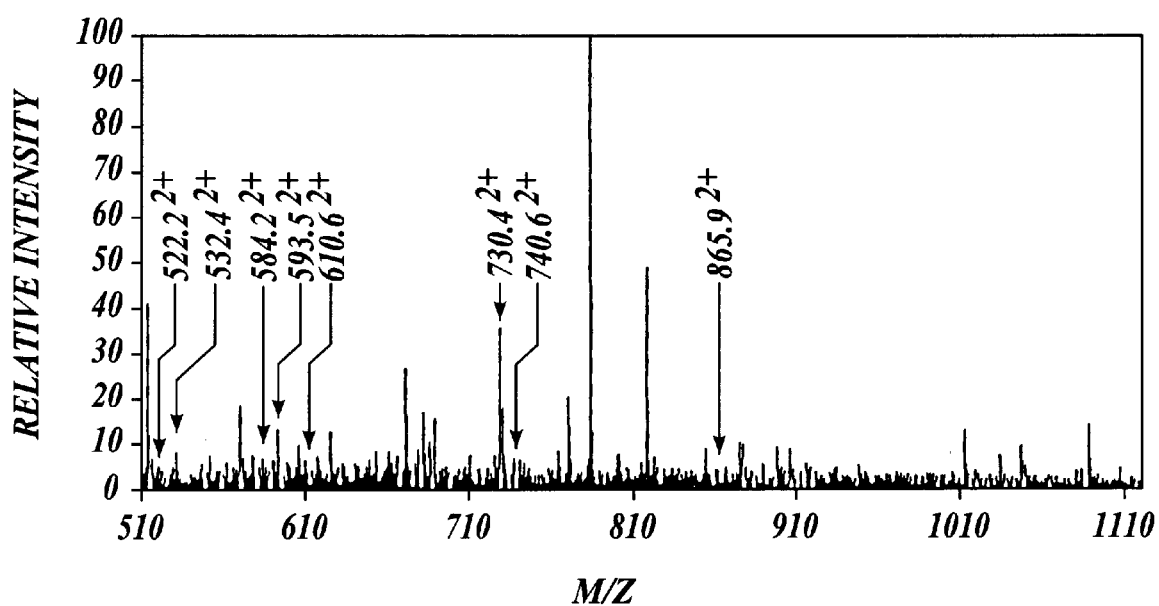
FIG. 10 is a mass spectrum obtained by a representative system of the invention for the tryptic digest of spot 14 shown in FIG. 9.

Protein identity was established by searching the yeast sequence database with the generated CID spectra using the Sequest search algorithm. The amount of protein present in the spots was determined to be in the range from 12 pmol (spot 1) to 180 fmol (spot 3) and sample concentrations ranged from an estimated 800 fmol/μl (spot 1) to 12 fmol/μl (spot 3). As a representative example, the MS data obtained from the analysis of spot 14 (from FIG. 9) are shown in FIG. 10. The eight peptides observed in FIG. 10 unambiguously identified the protein Heat Shock Protein 75. These results demonstrate the capability of the system of the invention to automatically and routinely identify protein samples at high sensitivity.

To summarize, in another aspect, the present invention provides an integrated, automated analytical system that includes a fluidics device microfabricated by photolithography/etching technology, an ESI-MS/MS system, an array of computer controlled high voltage relays for directing sample flows, and a data system for automated collection and analysis of MS/MS data. The system is an integrated system in which the sample flow as well as the analysis of the MS data have been automated under computer control. The system can be used to provide the automated, sensitive identification of proteins including, for example, proteins separated by 2DE.

The system and methods of the present invention are general, versatile and expandable and address some of the most difficult challenges in the analysis of trace amounts of biomolecules including sample contamination and sample loss. However, the use of microfabricated fluidic devices of specific function is not limited to protein identification. By adding affinity modules for the enrichment of analytes containing a specific structural determinant, the system can be expanded for the analysis of protein:ligand complexes and for the determination of protein modifications. The system arid methods of the invention are equally well suited for the conclusive analysis of analytes other than proteins and peptides. Compounds that are soluble in solvents compatible with ESI-MS/MS and produce diagnostic CID fragmentation patterns can be directed and analyzed by the system and methods of the invention.

Further improvements in the sensitivity of the system can be achieved by the use of transfer lines and ES ion sources of smaller inner diameter and by implementing solid phase extraction on-line with the microfabricated device. Furthermore, polymeric variants of such devices are cost effectively mass produced as routine sample feeds for high sensitivity ESI-MS/MS. The integration of sequential steps into a complete analytical process and the automation of process control and data analysis provided by the system of the invention render the system a practical analytical system of the future.

As described above, the fluidics device of the present invention can be widely configured and incorporated into a variety of systems that ultimately provide structural information for an analyte, for example, proteins, peptides, and complex mixtures thereof, through mass spectral analysis. Because the sensitivity achieved by ESI-MS is essentially dependent on the analyte concentration, the method of introducing the sample to the mass spectrometer system is critical. For high-sensitivity peptide analysis, two principally different sample application methods are commonly used.

The first method is the continuous application of an unseparated peptide mixture (i.e., nanospray technique). The nanospray technique has the advantage of extensive signal averaging over a long time for the analysis of selected sample constituents, thus improving the quality of the spectra obtained. Because the mass spectrometer only generates CID spectra of one analyte at a time, the other analytes present in the mixture go undetected during the analysis of the selected analyte and are therefore wasted. Other disadvantages of the nanospray technique are that no concentration of the analyte is achieved and that matrix effects affect the analysis of the analytes.

The second method is the sequential introduction of spatially separated peptides and consists of coupling spatial separation techniques such as HPLC or CE to the mass spectrometer. Concentration of analytes by up to a few orders of magnitude has been achieved. The separation technique presents analytes sequentially to the mass spectrometer and essentially eliminates global matrix effects. However, the time to perform the CID experiment is limited to the peak width of the analytes. Furthermore, the experiments are more technically difficult to perform and are only realizable if the MS/MS system used supports automated data-directed CID experiments.

In another aspect, the present invention provides temporal separation of analytes (without spatial separation) as a third principle for introducing peptides to a micro- or nano-ESI MS system. Temporal analyte separation is achieved by the generation of solvent gradients on a fluidic device and the sequential mobilization of peptides immobilized on a SPE cartridge by frontal analysis. The mobilized peptides are then identified by a mass spectrometer, preferably by MS/MS in an ion trap mass spectrometer. The advantages of this technique are the separation and concentration of analytes, elimination of matrix effects, and controllable time of analysis.

Figure 11A:
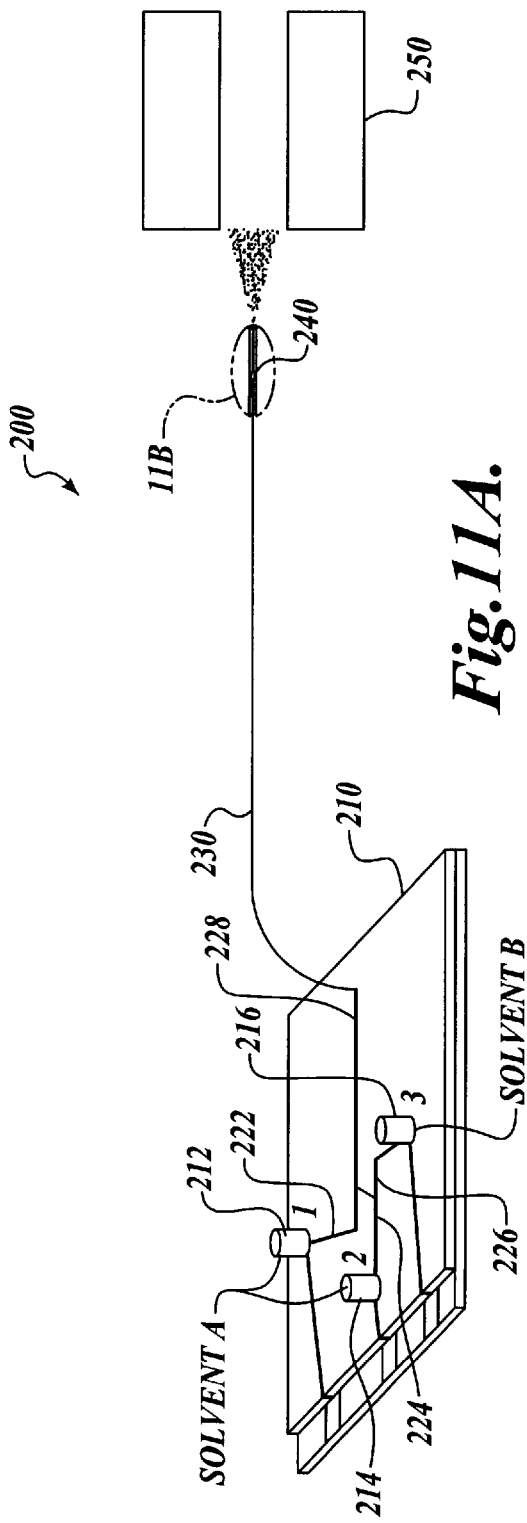
FIG. 11 is a schematic diagram of a representative system of the present invention including a representative three-position fluidics device coupled to a mass spectrometer by a transfer capillary and a microelectrospray ionization interface, a solid phase cartridge is incorporated into the interface.
Figure 11B:
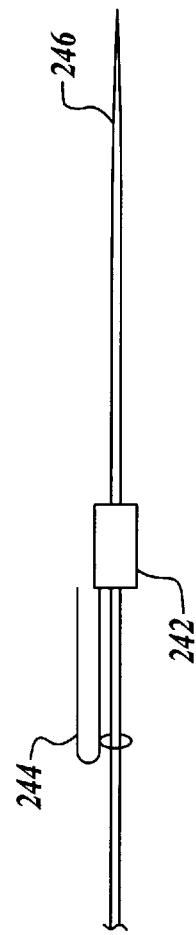

The present invention provides a fluidic device, preferably a microfabricated device, that can generate and deliver solvent gradients at nanoliter per minute flow rates. The solvent gradients are achieved by directed differential electroosmotic pumping of, for example, an aqueous and an organic phase, respectively, present in different reservoirs on the device. Differential electroosmotic pumping is achieved by varying the potential applied to the respective reservoirs. In one embodiment, the solvent gradient device is combined with a solid-phase extraction (SPE) cartridge, for example, a C18 cartridge, for the separation by frontal analysis of peptides present in complex peptide mixtures. The peptides loaded onto the cartridge are eluted from the cartridge by the solvent gradient generated by and delivered from the fluidic device and then identified by an ESI-ion trap mass spectrometer. Such a system is schematically illustrated in FIG. 11.

The fluidic devices of the present invention are well suited for the generation of solvent gradients as multiple reservoirs and flow paths can be present on a single device and can be individually addressed. In the invention, electroosmotically generated flows from specific reservoirs can be joined in a controlled fashion to generate solvent gradients. The magnitude and the direction of the electroosmotic flows are controlled by the potentials applied to the reservoirs.

The fluidic device generally as described above can be used to generate and deliver solvent gradients. In a representative 3-position fluidic device (see, e.g., FIG. 1), channels (30 $\mu$m depth×72–73 $\mu$m width) and three reservoirs (1 mm×1 mm) were etched on a piece of glass (540 $\mu$m thick) to provide a device as shown in FIG. 11. Referring to FIG. 11, System 200 includes three-position fluidics device 210 that includes reservoirs 212, 214, and 216, each containing an electrode connected by a metal line to a contact pad. Reservoirs 212, 214, and 216 are connected by channels 222, 224, and 226, respectively, to channel 228 which directs sample flow from the fluidics device to transfer capillary 230, which also serves as the electroosmotic pump. Transfer capillary 230 directs liquid sample to liquid junction microESI interface 240, which includes, in one embodiment, solid phase extraction cartridge 242, a metal wire 244 inserted in the cartridge for electrical contact and connected to the power supply of the mass spectrometer to which the interface was coupled, and electrospray needle 246. Interface 240 is coupled to a mass spectrometer through entrance 250.

In one embodiment, the link between device 210 and transfer capillary 230 was made perpendicular to the plane of the device. The link was made by inserting a 200 $\mu$m i.d.×350 $\mu$m o.d. sheath capillary in the 350 $\mu$m hole drilled at the end of the main channel and gluing it in place using heat-curable epoxy. A 250 μm i.d. and 1.5 mm o.d. TEFLON tube was inserted over the sheath capillary and glued in place. A small section of the TEFLON tube had been previously expanded to fit the full length of 350 μm o.d. of the sheath capillary. A fingertight fitting was added to the other end of the TEFLON tubing. A transfer capillary was inserted into the TEFLON tube and into the sheath capillary so that its end reached to the etched channel on the microfabricated device. The transfer capillary was held in place by tightening the fingertight fitting. The 15-cm-long transfer fused-silica capillary (50 μm i.d.×150 μm o.d.) served as a connection between device 210 and liquid junction microESI interface 240. Bare fused silica or capillaries derivatized with (3-aminopropyl)silane can be used.

In one embodiment, the liquid junction includes a solid phase extraction cartridge as shown in FIG. 11. In this embodiment, the transfer capillary was inserted with a small platinum wire midway through another 250 μm i.d. TEFLON tube and glued in place using 5-minute epoxy. A small piece of membrane followed by a 1–3 mm long bed of C18 resin and another piece of membrane were inserted from the other end of the TEFLON tubing. Finally, a microESI needle, made from a 50-μm i.d. and 150-μm o.d. fused silica capillary, which was tapered in a flame, was inserted and glued in place. This liquid junction interface was positioned with the microESI needle facing the entrance of the mass spectrometer. The potential for the ESI process was supplied by the power supply of the ion trap mass spectrometer and applied through the small platinum wire of the microESI interface. A constant voltage of +1.3 to +1.7 kV was applied for the duration of an experiment.

The samples were pressure loaded on the SPE device in the liquid junction interface. The loading was performed by disconnecting the transfer line from the device and inserting it into a pressurizable microvial. The samples were generally loaded at 6–9 psi for up to 10 min. allowing a loading of about 10–20 μL of sample. Once the samples were applied, the column was rinsed and equilibrated with 10 mM acetic acid/10% methanol and the transfer capillary was reconnected to the device.

The gradients were generated by controlled electroosmotic pumping from two reservoirs filled with different solvents. For example, reservoir one was filled with 10 mM acetic acid/10% methanol (v/v) (solvent A), reservoir two, although not used for the experiment, was filled with the same solvent, and reservoir three was filled with 65% acetonitrile (v/v)/10 mM acetic acid (solvent B). Platinum electrodes connected to individual power supplies were inserted into reservoirs one and three, respectively. The gradient was generated by ramping potentials to reservoirs one and three. In a typical experiment, reservoir one was held to −5.2 kV while the potential of reservoir three was ramped from −4.6 to −5.2 kV over 14 min. Then, the potential of reservoir one was ramped from −5.2 to 4.5 or −4.2 kV over 14 min, while reservoir three was maintained at −5.2 kV. Finally, both reservoirs were kept at these final voltages for the rest of the experiment. The columns were reequilibrated by switching reservoir one back to −5.2 kV and reservoir three to −4.5 kV.

Gradients were generated on the system described in FIG. 11 by ramping potentials to reservoirs one and three. For these experiments, a bare fused-silica capillary was used as transfer capillary. Reservoir one was filled with 10 mM acetic acid/10% (v/v) methanol and reservoir three was filled with 65% (v/v) acetonitrile/3 mM acetic acid. The difference in potential between the reservoirs and the microelectrosprayer-generated electroosmotic flows toward the microelectrosprayer, and therefore, solvent gradients were generated without the need for a pump. Two high voltage power supplies were used to furnish the appropriate potential to reservoirs one and three. Each power supply was controlled through a digital to analog converter board (DAC) and a Labview procedure. This procedure controlled the potential (0–10 V) applied to two analog outputs of the DAC which in turn controlled the high voltage power supply. This procedure ramped the potential applied to the DAC output according to preset initial and final voltages and ramping times.

Figure 12A:
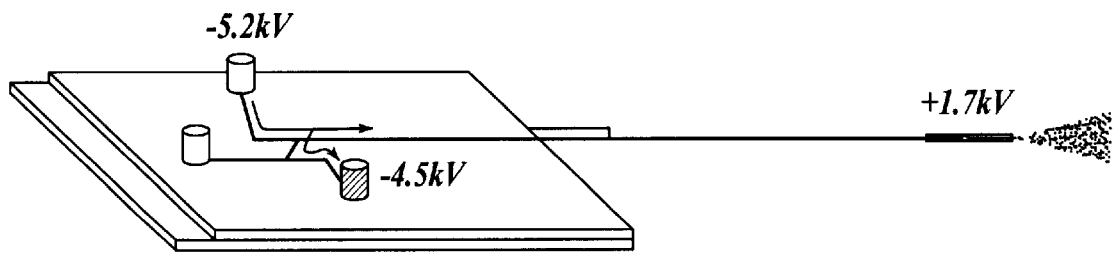
FIGS. 12A–12C are flow diagrams illustrating the generation of a solvent gradient by a representative method of the present invention.
Figure 12B:
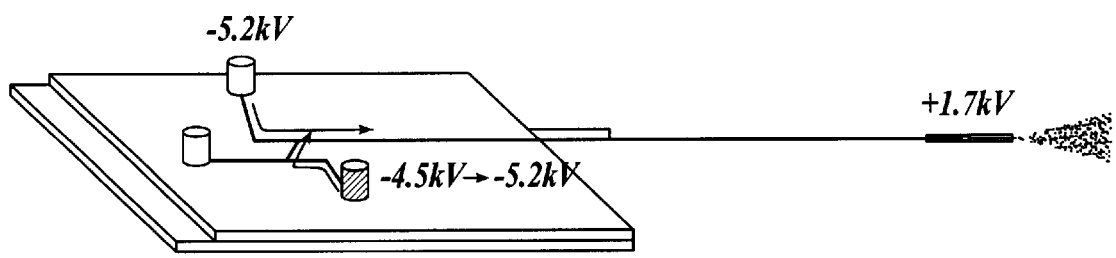
Figure 12C:
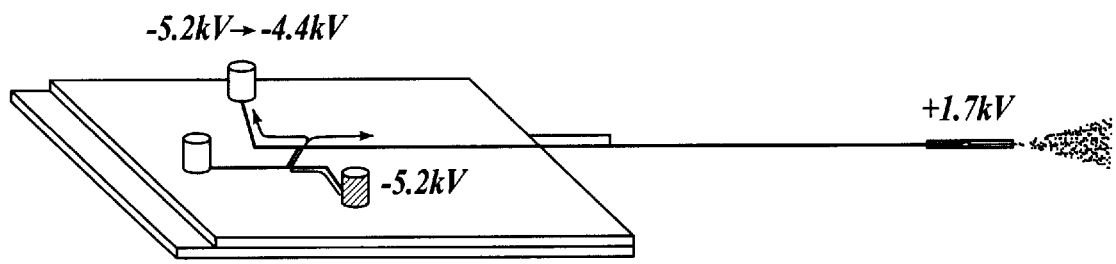

The generated gradients were followed by monitoring in the mass spectrometer a signal representing the clustering of acetonitrile. The signal increased as the acetonitrile concentration increased. The course of a typical experiment for generating an aqueous/organic solvent gradient is illustrated in FIGS. 12A–12C. At the start of an experiment, reservoir one was held at −5.2 kV and reservoir three was held at −4.5 kV (see FIG. 12A). This generated a forward flow from reservoir one to the microESI and back in reservoir three. The small secondary flow from reservoir one to reservoir three ensured that only the buffer from reservoir one reached the micro ESI interface.

In a second phase (see FIG. 12B), the potential on reservoir three was ramped up from −4.5 to −5.2 kV over 14 min. At the same time, the potential on reservoir one was held constant. During this phase, the flow from reservoir one to reservoir three slowly decreased. At a certain potential value, at which the potential on reservoir three was higher than the potential at the junction of the flow path from reservoirs one and three, no flow was apparent from reservoir three. At higher potential values an increasing flow from reservoir three toward the microESI interface was generated. The net effect of this step was an increase in the acetonitrile concentration flowing toward the mass spectrometer.

In a third phase (see FIG. 12C), the potential on reservoir one was slowly increased from −5.2 to −4.2 or −4.4 kV over 14 min and the potential on reservoir three was kept constant at −5.2 kV. During this ramping, the flow from reservoir one slowly decreased. At a certain point, the flow from reservoir one stopped and then reversed into reservoir one from reservoir three.

Figure 13A:
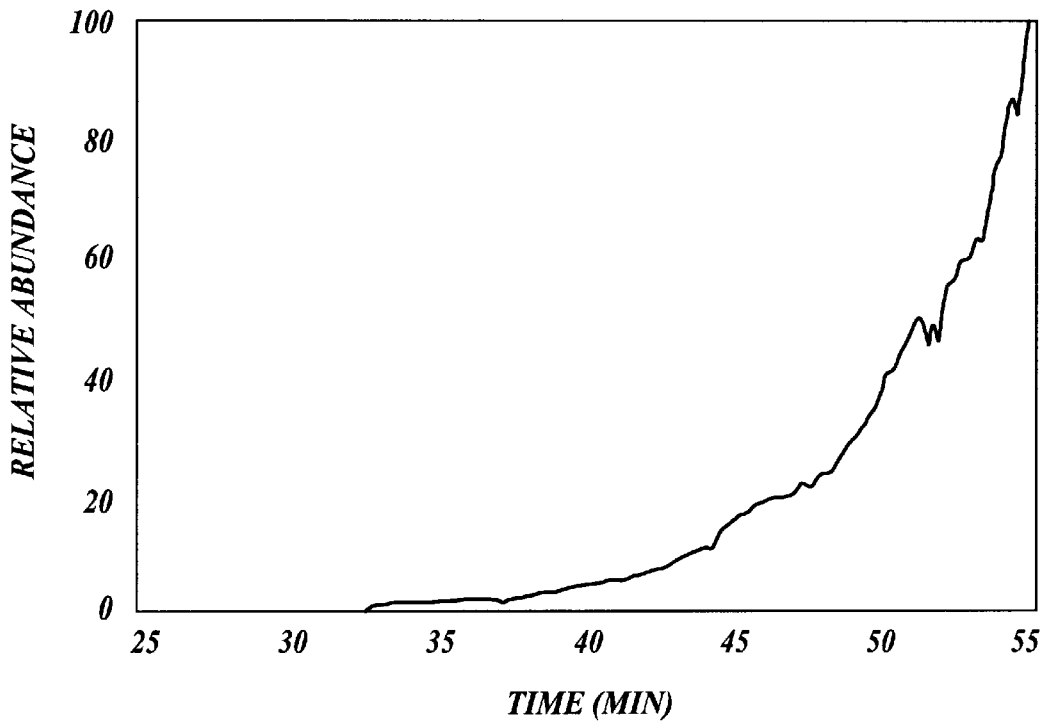
FIGS. 13A and 13B are illustrations of solvent gradient profiles generated by the system shown in FIG. 11 and the method illustrated in FIG. 12.
Figure 13B:
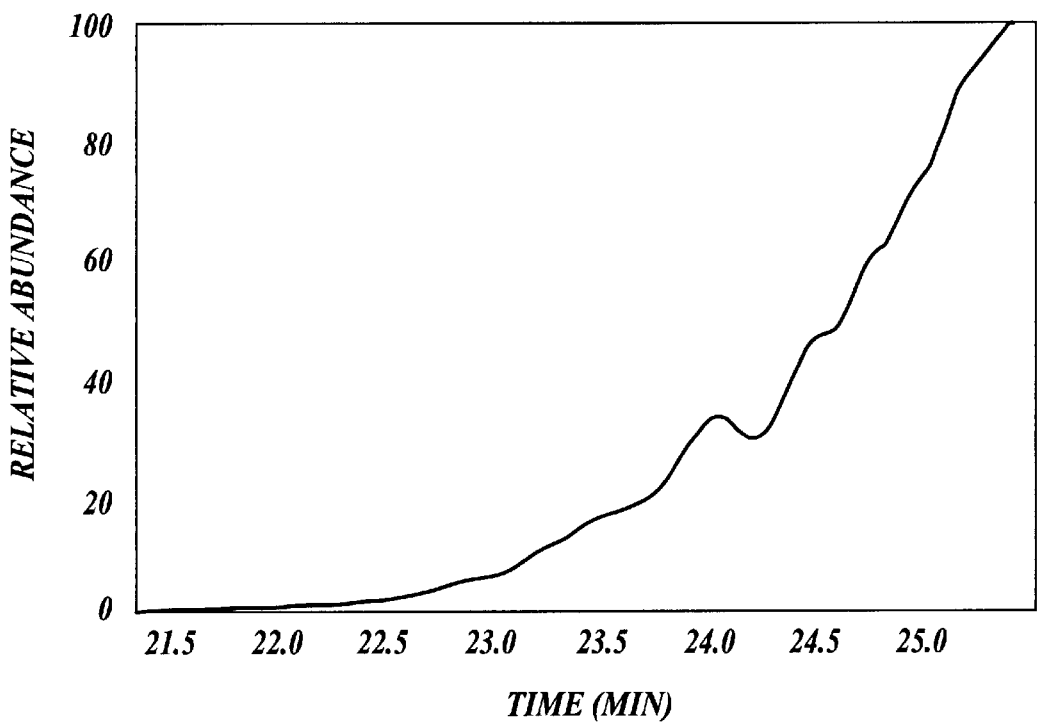

FIGS. 13A and 13B illustrate representative solvent gradients generated and delivered by the device and method of the invention. The gradient is well described with an exponential equation. The gradient started at 28 min and finished at 50 min. thus providing 22 min for a gradient to develop from 0 to 65% acetonitrile.

The change in the solvent composition over the course of an experiment was also apparent from the current delivered by the power supply. During the formation of a gradient, the ionic composition of the solution in the channels of the device and in the transfer capillary changed. The current supplied by the microESI power supply was the summation of the current from the microfabricated device and the current for the electrospray ionization process. Changes in ionic composition in the channels of the microfabricated device and in the transfer capillary were therefore reflected by changes in the current provided by the mass spectrometer high voltage power supply. In the first phase of the experiment, the current provided by the mass spectrometer power supply was stable, reflecting a stable ionic composition of aqueous buffer in the channels and in the transfer capillary. In the second phase, the current provided by the microESI power supply started to drop, due to the difference in conductivity between the solutions in reservoirs one and three, indicating an increasing concentration of acetonitrile present in the channels and transfer capillary. In the third phase, the current continued to drop and eventually reached a plateau reflecting a stable acetonitrile concentration in the channels and transfer capillary.

Typically, the shapes of the gradients were similar for all the experiments done with the same capillary. However, the starting point and end point of the gradient were influenced by the size and the compression state of the C18 cartridge. As the size of the cartridge increased, the flow restriction also increased. Similarly, as the compression of the beads increased, the flow restriction increased and the onset of the gradient was delayed.

The onset and shape of the gradient are expected to depend on the flow rate of the solvent. The effect on the gradient generated was evaluated by replacing the, bare silica transfer capillary with an (aminopropyl)-silane-coated transfer capillary. At pH 3.0, the inner surface of this coated capillary is protonated and generates a strong electroosmotic flow toward the microESI. The gradient generated using a coating capillary under conditions otherwise identical to the ones described above is shown in FIG. 13B. Because the electroosmotic pumping was stronger, the gradient started earlier and was sharper compared to the bare fused-silica capillary. The gradient started at 20 min and was finished by 25 min. The result indicates that the shape, slope, and direction of the gradient can be controlled by various parameters, including the control of the voltages applied to the reservoirs and the surface chemistry of the transfer capillary.

The incorporation of a solid phase for immobilizing an analyte onto or downstream from the device provides for a system and method suitable for the concentration and frontal analysis of protein digests by mass spectrometry. The system and method advantageously include the use of a solvent gradient formed by the fluidic device.

The ion trap mass spectrometer was used essentially as described above with the following modifications. The trap was run with automatic gain control for all experiments. In this mode, the system automatically selects the gating parameters to keep the number of ions present in the trap to a constant preset value. In MS mode, the target number of ions was set to $1 \times 10^8$, and in CID mode, to $2 \times 10^7$. The electron multiplier was set to $-1060$ V. Three sequential scan ranges were used in the MS mode: from 400 to 725; from 725 to 1000; and from 1000 to 1850 amu, respectively. The most intense ion from each scan range was selected with a 3 amu window, and CID experiments were performed with the energy set at 55%, the maximum trap time set at 1500 ms and the number of microscans set to 7. All the spectra were recorded in centroid mode.

The MS/MS spectra were searched against protein databases using the Sequest software to identify the source of the peptides.

Figure 14:
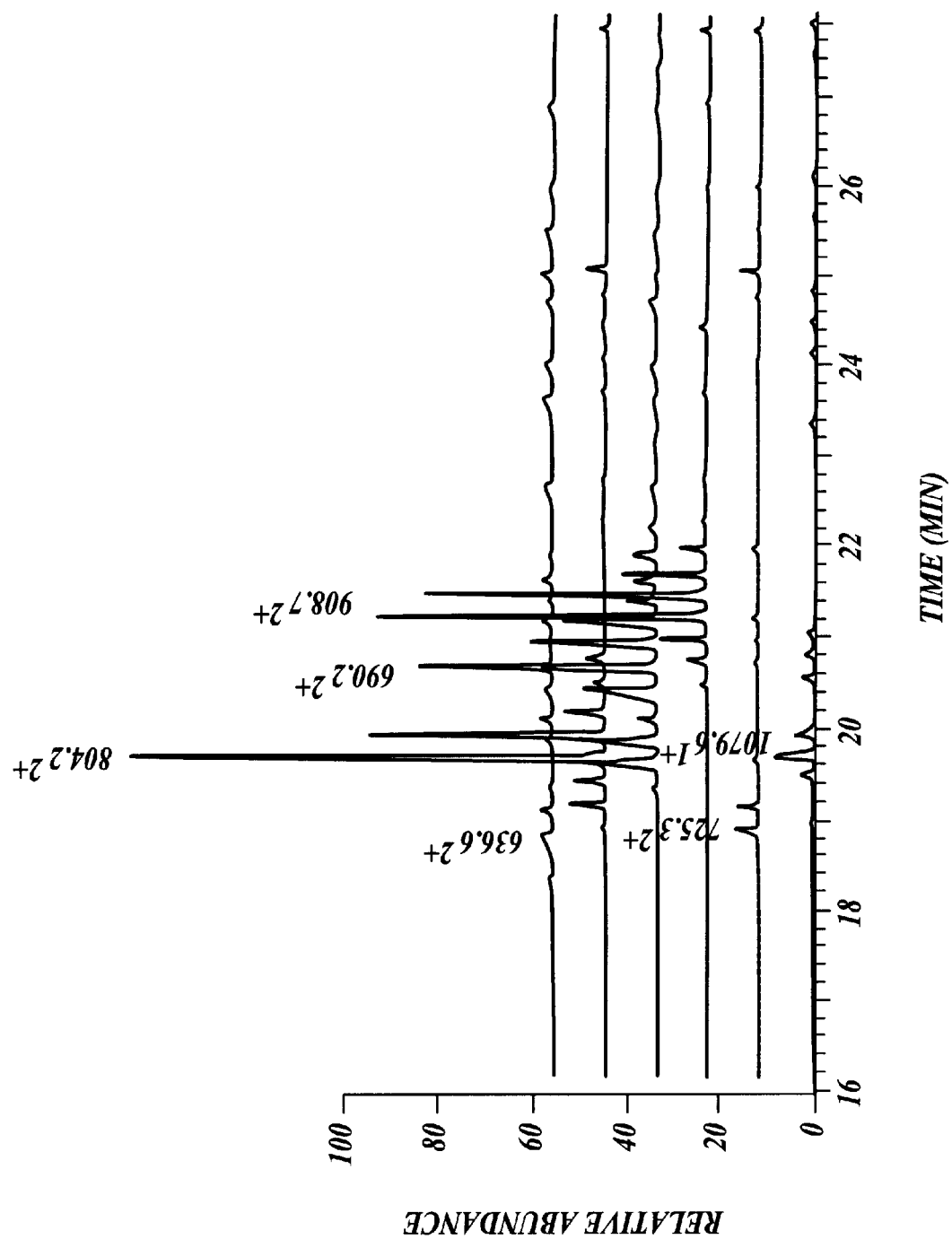
FIG. 14 illustrates the analysis of a myoglobin tryptic digest by gradient frontal analysis-MS/MS by the method illustrated in FIG. 12 using a (3-aminopropyl)silane-coated transfer capillary.

A standardized solution of myoglobin digested with trypsin was analyzed using the fluidic device described above coupled to a mass spectrometer. FIG. 14 illustrates the analysis of a 10-$\mu$L aliquot of 7.4 fmol/$\mu$L (total 74 fmol) tryptic digested myoglobin on the gradient system equipped with a derivatized transfer capillary. The sample was pres sure loaded (6–9 psi) off-line. The transfer capillary was then reconnected to the microfluidic device, and the gradient was developed. Peptides eluted from the C18 cartridge were detected by the mass spectrometer. If a specific peptide ion exceeded a predetermined intensity, the instrument automatically switched to MS/MS mode and the resulting CID spectra were recorded. These spectra were used in conjunction with the Sequest program to search a horse protein sequence database to identify the origin of the peptides. The control of the high voltage power supply and the generation of CID spectra were performed automatically using a Labview procedure and a method developed with the software provided with the mass spectrometer. The trace of the intensity versus time for each one of the identified peptides was recreated and displayed in FIG. 14. The drop in intensity in the profiles is due to the mass spectrometer continuously switching from MS to MS/MS mode. The secondary peaks. are artifacts caused by daughters product ions from other precursor ions that have the same m/z as the identified peptides. Six peptides were identified as being derived from myoglobin. Other peptides from myoglobin were also present. These peptides did not generate CID spectra of good enough quality for unambiguous identification or were small peptides with a 1+ charge. Such spectra were not assigned by the Sequest software. This experiment was repeated at least three times with different solutions of trypsinized myoglobin and similar results were obtained each time The detected peaks are not chromatographic peaks but represent a frontal analysis performed on a small column. Therefore, the peak widths are a function of the gradient shape and the peptide diffusion coefficients. The signal intensity was well above the background signal. Using the signal from the peptide ion at m/z=$804.2^{2+}$ and a noise value calculated as three times the average background signal in a mass window 20 Da below the detected peptide ion, a limit of detection of 1 fmol and a concentration LOD of 100 amol/$\mu$L, assuming that 10 $\mu$L of sample was applied to the C18 cartridge.

The analysis of unknown proteins separated by standard techniques, such as 1D and 2D gel electrophoresis, was performed using the system of the present invention. *Saccharomyces cerevisiae* was selected as the source of the proteins because the complete genome sequence is available, and therefore, the CID spectra of each peptide are expected to match to the sequence database.

Figure 15:
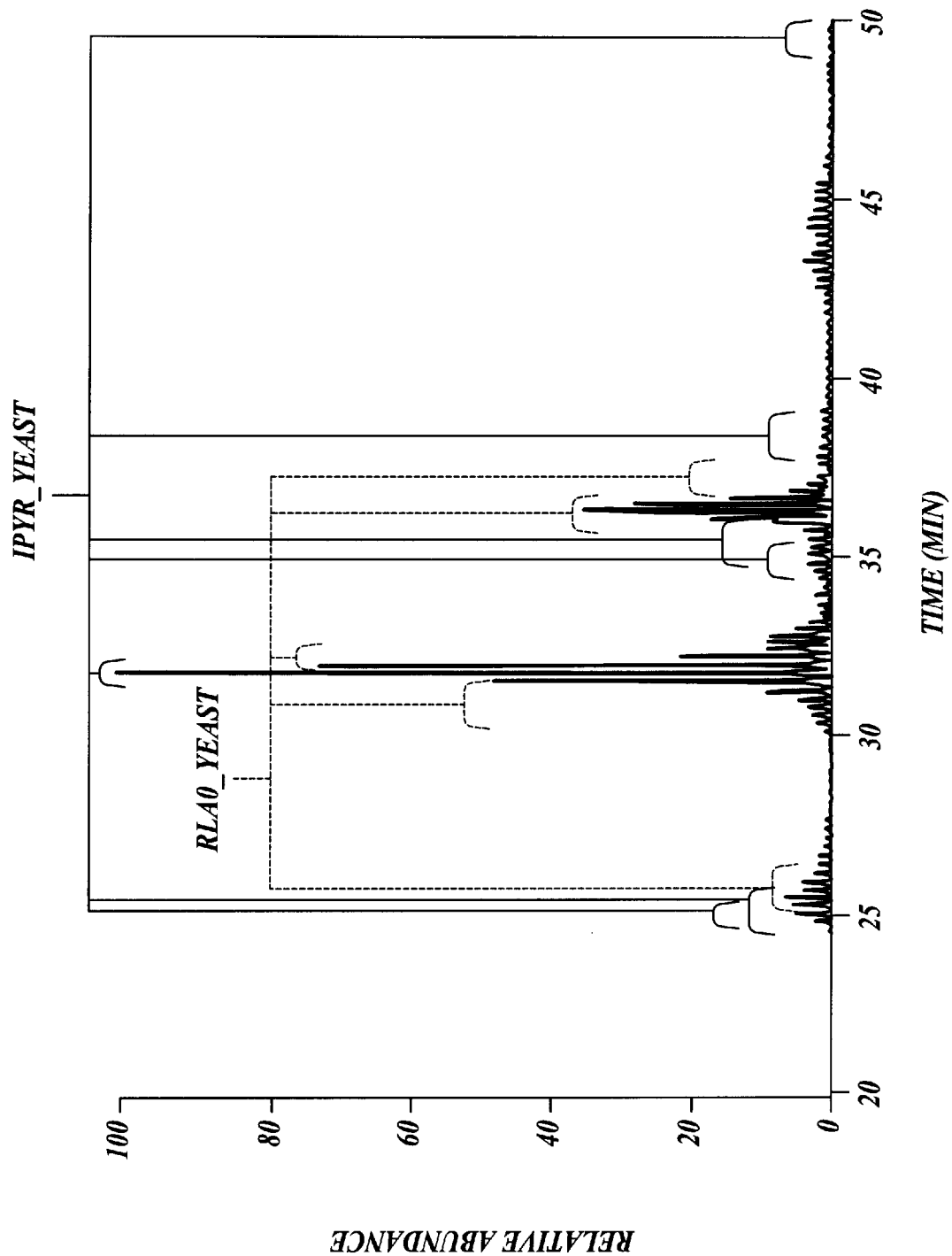
FIG. 15 illustrates the analysis of a band of yeast proteins separated by 1D gel electrophoresis of yeast total cell lysate digested with trypsin analyzed by gradient frontal analysis-MS/MS by the method illustrated in FIG. 12 using an uncoated transfer capillary.

Tryptic digests of protein bands obtained from a 1D gel electrophoresis separation of total yeast lysate were analyzed. FIG. 15 shows the frontal analysis of a tryptic digest of a sample representing a single band migrating at 34 kDa in the gel that was extracted from the gel. The sample was pressure loaded off-line on the C18 cartridge. The transfer capillary was then reconnected to the microfabricated device, and the gradient was generated. CID spectra of the eluted peptides were generated on the fly. The signal intensity was a few orders of magnitude above the limit of detection. Six different proteins were identified as being present in this band with up to seven peptides identifying a specific protein. The results from the search of the CID spectra against a yeast protein sequence database using the Sequest software are summarized in Table 4. All the peptides identified had a Xcorr higher than 2.0, which indicates a confident match to the sequence database.

TABLE 4

Peptides identified by the Sequest Software during the Analysis of a 34 kDa Band Digest by Gradient Frontal Analysis MS/MS

| [MH]+ | Xcorr | Sequence | Protein |
|---|---|---|---|
| 1148.7 | 3.0 | (R)VVDLIEYVAK (SEQ ID NO: 28) | G3P1 |
| 1197.6 | 2.5 | (R)DPANLPWGSLK (SEQ ID NO: 29) | G3P1 |
| 1470.8 | 3.8 | (R)VPTVDVSVVDLTVK (SEQ ID NO: 30) | G3P1, G3P2, G3P3 |
| 1845.9 | 4.3 | (K)VINDAFGIEEGLMTTVH (SEQ ID NO: 31) | G3P1, G3P2, G3P3 |
| 2593.3 | 3.3 | (K)VINDAFGIEEGLMTTVHSMTATQK (SEQ ID NO: 32) | G3P1, G3P2 |
| 2403.2 | 5.7 | (K)DPANLPWGSSNVDIAIDSTGVFK (SEQ ID NO: 33) | G3P3 |
| 2631.3 | 5.1 | (K)PNVEVVALNDPFTTNDYAAYMFK (SEQ ID NO: 34) | G3P3 |
| 2575.3 | 4.3 | (K)VINDAFGIEEGLMTTVHSLTATQK (SEQ ID NO: 35) | G3P3 |
| 2207.1 | 3.5 | (K)VVITAPSSTAPMFVMGVNEEK (SEQ ID NO: 36) | G3P2, G3P3 |
| 1752.8 | 3.1 | (K)LVSWYDNEYGYSTR (SEQ ID NO: 37) | G3P2, G3P3 |
| 1539.7 | 2.4 | (S)STAPMFVMGVNEEK (SEQ ID NO: 38) | G3P2, G3P3 |
| 1400.7 | 2.4 | (K)EETLNPIIQDTK (SEQ ID NO: 39) | IPYR |
| 1834.9 | 3.2 | (K)IPDGKPENQFAFSGEAK (SEQ ID NO: 40) | IPYR |
| 1985.1 | 3.4 | (K)LEITKEETLNPIIQDTK (SEQ ID NO: 41) | IPYR |
| 1378.8 | 3.0 | (K)VIAIDINDPLAPK (SEQ ID NO: 42) | IPYR |
| 1834.9 | 3.4 | (K)GIDLTNVTLPDTPTYSK (SEQ ID NO: 43) | IPYR |
| 1574.8 | 3.0 | (K)ENNIFNMVVEIPR (SEQ ID NO: 44) | IPYR |
| 2517.3 | 4.9 | (K)AVGDNDPIDVLEIGETIAYTGQVK (SEQ ID NO: 45) | IPYR |
| 1267.6 | 2.3 | (K)GFLSDLPDFEK (SEQ ID NO: 46) | RLA0 |
| 1295.7 | 3.5 | (K)TSFFQALGVPTK (SEQ ID NO: 47) | RLA0 |
| 2131.3 | 2.6 | (K)SLFVVGVDNVSSQQMHEVR (SEQ ID NO: 48) | RLA0 |
| 1283.7 | 3.9 | (R)AGAVAPEDIWVR (SEQ ID NO: 49) | RLA0 |
| 1060.6 | 2.0 | (R)GTIEIVSDVK (SEQ ID NO: 50) | RLA0 |
| 1834.0 | 3.3 | (K)TASEIATTELPPTHPIR (SEQ ID NO: 51) | BMH1, BMH2 |
| 1476.0 | 3.6 | (R)FLEQQNQVLQTK (SEQ ID NO: 52) | K2C1 human |
| 1718.0 | 4.2 | (K)QISNLQQSISDAEQR (SEQ ID NO: 53) | K2C1 human |
| 1358.3 | 4.1 | (R)LNDLEDALQQAK (SEQ ID NO: 54) | K2C1 human |
| 1383.7 | 2.9 | (K)SLNNQFASFIDK (SEQ ID NO: 55) | K2C1 human |
| 3266.1 | 5.9 | (K)DIENQYETQITQIEHEVSSSGQEVQSSAK (SEQ ID NO: 56) | K2C1 human |
| 2211.1 | 5.2 | (K)LGEHNIDVLEGNEQFINAAK (SEQ ID NO: 57) | K1C1 human |

Only one peptide was matched with proteins BMH1/BMH2. Because of the quality of the database match and the match of the observed and calculated molecular weight of BMH1/BMH 2 (29,960/30,930). The proteins are included in the list of positively identified proteins. The acetonitrile cluster signal used to document the gradient in FIG. 13 was not visible in FIG. 15 because of the way the data were displayed. Furthermore, not all the peaks present in FIG. 15 contained peptides. Some peaks were due to other chemicals present in the sample and others were artifacts caused by the continuous switching of the mass spectrometer between MS mode and MS/MS mode. Peptides from keratin and trypsin were also observed but were not labeled in FIG. 15 and are added to Table 4 for clarity. These results clearly demonstrate that this system can be used to deconvolute a complex mixture of peptides at high sensitivity and in an automated manner.

Figure 16:
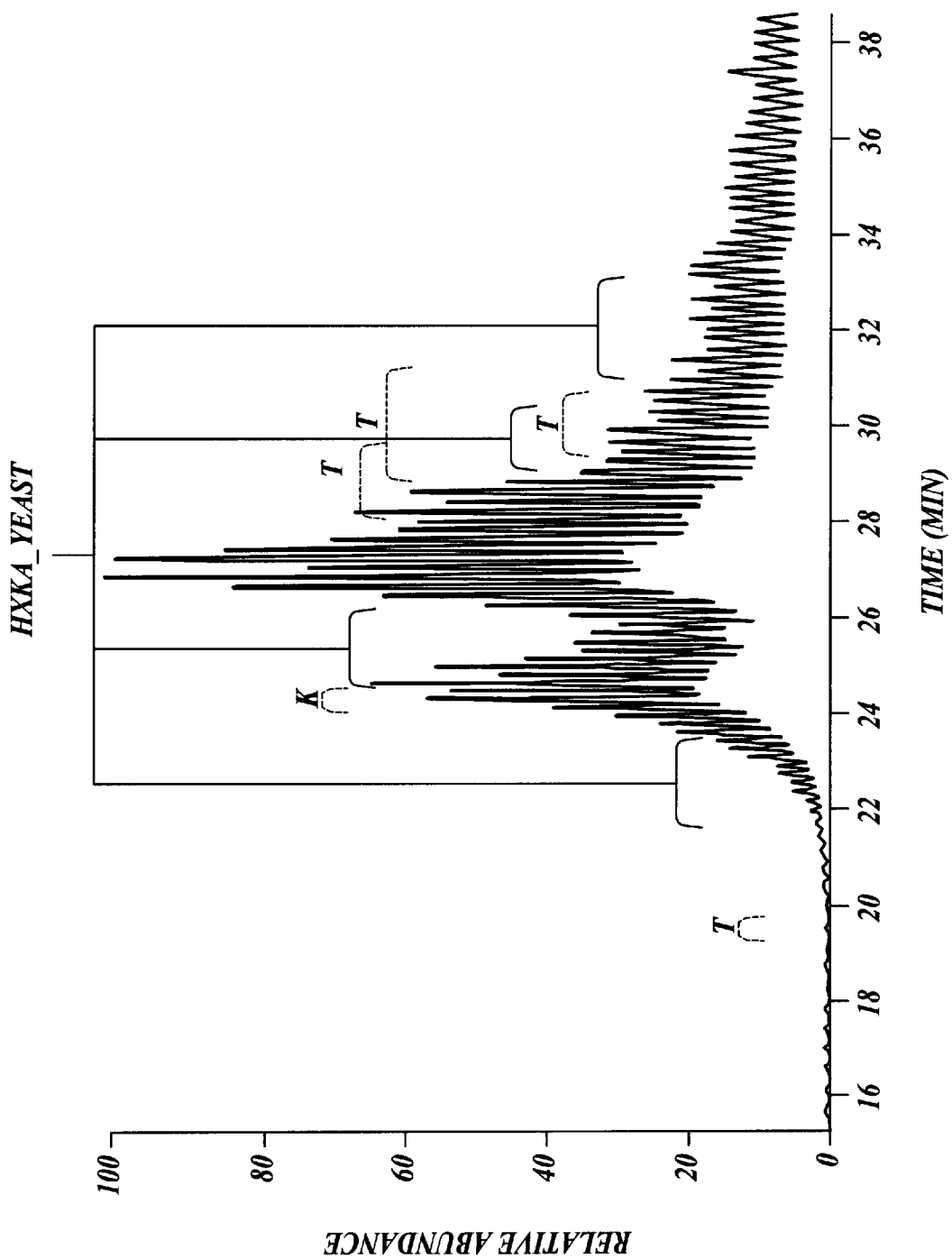
FIG. 16 illustrates the analysis of a spot of yeast protein separated by 2D gel electrophoresis of yeast total cell lysate digested with trypsin analyzed by gradient frontal analysis-MS/MS by the method illustrated in FIG. 12 using a (3-aminoproyl)silane-coated transfer capillary.

Proteins obtained from a 2D gel separation of a total yeast lysate were also analyzed. A representative analysis of the protein in a selected spot is presented in FIG. 16. Four peptides were identified as being from HXKA yeast along with one peptide from keratin and four peptides from trypsin. The results from the search of the CID spectra against the yeast protein database are summarized in Table 5. All the peptides identified had a Xcorr higher than 2.0 except for [MH]$^+$=630.4 which was a small peptide observed as a 1$^+$ ion. The amount of protein present in the gel was estimated to be about 200–300 fmol.

TABLE 5

Peptides Identified by the Sequest Software during the Analysis of a Single Spot from a Yeast 2D Gel by Gradient Frontal Analysis MS/MS

| [MH]$^+$ | Xcorr | Sequence | Protein |
|---|---|---|---|
| 943.0 | 3.1 | (K)INEGILQR (SEQ ID NO: 58) | HXKA |
| 1886.5 | 3.1 | (K)DTLPLGFTTFSYPASQNK (SEQ ID NO: 59) | HXKA |
| 2419.6 | 3.5 | (K)GFDIIPNVEGHDVVPLLQNEISK (SEQ ID NO: 60) | HXKA |
| 630.4 | 1.6 | (K)SLGIIGA (SEQ ID NO: 61) | HXKA |
| 1940.9 | 2.3 | (R)LGEHNIDVLEGNEQFIN (SEQ ID NO: 62) | TRYP pig |
| 2299.2 | 3.7 | (K)IITHPNFNGNTLDNDIXIK (SEQ ID NO: 63) | TRYP pig |
| 2284.9 | 3.3 | (K)IITHPNFNGNTLDNDIMLIK (SEQ ID NO: 64) | TRYP pig |
| 2210.6 | 4.4 | (R)LGEHNIDVLEGNEQFINAAK (SEQ ID NO: 65) | TRYP pig |
| 1475.4 | 4.8 | (R)FLEQQNQVLQTK (SEQ ID NO: 66) | K2C1 human |

To summarize, in one aspect, the present invention provides a fluidics device for the generation of solvent gradients which sequentially elute peptides absorbed on a SPE cartridge. The system can be used for frontal analysis of complex peptide mixtures and the analysis on-line of the separated peptides by MS/MS and for the analysis of protein digests. The system has a limit of detection in the low-femtomole level and can be used for high sensitivity protein analysis by identifying yeast proteins separated by 1D and 2D gel electrophoresis.

The following chemicals, materials, and instrumentation were used to make and evaluate the devices and methods of the invention. Acetic acid, acetonitrile and methanol were from J. T. Baker (Phillipsburg, N.J.). Sequencing grade modified trypsin (porcine) was from Promega (Madison, Wis.). Bovine serum albumin (BSA), carbonic anhydrase (CA), βlac, horse myoglobin (Mb), human haptoglobin 2-1 (Hg) and fibrinopeptide A were obtained from Sigma Chemical Company (St. Louis, Mo.). The concentration of βlac was calibrated by amino acid analysis. The fused silica capillary tubing was from Polymicro Technologies (Phoenix, Ariz.). TEFLON sleeves and finger tight fittings were from Upchurch Scientific (Oak Harbor, Wash.). TEFLON tube-dual shrink and stainless steel tubing were from Small Parts (Miamilakes, Fla.). Rapidly hardening epoxy glue was from Devcon Corporation (Danvers, Mass.), UV curable glue from Norland Products (New Brunswick, N.J.), epoxies were from ETC (Greenville, R.I.), and temperature-curved epoxy (H77I) and one phase epoxy (Epotek 115mst, EpoxyTechnology, Billerica, Mass.). Distilled water was deionized (18 MΩ) using a Milli-Q system from Millipore (Bedford, Mass.). The 5 μm diameter 300 Å pore size C18 material was from Phase Separations (Norwalk, Conn.). CE high-voltage power supplies were purchased from Spellman (Plainview, N.Y.). The LCQ ion trap MS was a product of Finnigan Mat (San Jose, Calif.).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for generating a solvent gradient, comprising:
   (a) providing a fluid path from a fluidic device to a counterelectrode, wherein the device comprises a plurality of reservoirs each containing a liquid, a fluid exit for directing liquid to the counterelectrode, wherein each reservoir is connected by a channel to a common channel for conducting liquid from each reservoir to the fluid exit, and wherein each reservoir further comprises an electrode in electrical contact with the liquid in the reservoir;
   (b) applying a first voltage to the counterelectrode;
   (c) applying a second voltage to a first electrode in a first reservoir to generate a difference in potential between the first electrode and the counterelectrode, wherein the difference in potential causes migration of a first liquid from the first reservoir to the common channel;
   (d) applying a third voltage to a second electrode in a second reservoir to generate a difference in potential between the second electrode and the counterelectrode, wherein the difference in potential causes migration of a second liquid from the second reservoir to the common channel, wherein the first and second liquids are combined in the common channel to provide a solvent gradient comprising a combination of the first and second liquids; and
   (e) wherein applying voltages to the first and second electrodes comprises:
      (i) applying an initial constant voltage to the first electrode and an initial constant slightly lower voltage to the second electrode;
      (ii) ramping the initial voltage applied to the second electrode to about the initial voltage applied to the first electrode and holding the second electrode constant at that voltage; and
      (iii) ramping the initial voltage applied to the first electrode to about the initial voltage applied to the second electrode and holding the first electrode constant at that voltage.

2. The method of claim 1 wherein the counterelectrode comprises an electrospray needle of an electrospray ionization source.

3. The method of claim 2 wherein the voltage applied to the electrospray needle is in the range from about +1.5 to about +2.0 kV.

4. The method of claim 1 wherein the fluid path from the fluidic device to the counterelectrode further comprises a capillary.

5. The method of claim 1 wherein the voltages applied to the electrodes are in the range from about −2 to −8 kV.

6. The method of claim 1 further comprising delivering the solvent gradient from the device.

7. The method of claim 6 wherein the solvent gradient is delivered at a flowrate in the range of from about 1 to about 100 nanoliters per minute.

8. The method of claim 1 wherein the solvent gradient is delivered to a sample immobilized on a solid phase.

9. The method of claim 8 wherein the solid phase is on the fluidic device.

10. The method of claim 8 wherein the solid phase is at a position between the fluidic device and the counterelectrode.

11. The method of claim 8 wherein a sample comprises an analyte that can be mobilized by the solvent gradient.

12. The method of claim 11 further comprising directing the mobilized analyte to an electrospray ionization source, ionizing the analyte to provide an ionized analyte, introducing the ionized analyte into a mass analyzer, and identifying the analyte.

13. The method of claim 12 wherein the analyte is selected from the group consisting of a protein and peptide.

14. The method of claim 12 wherein the mass analyzer is a tandem mass spectrometer.

* * * * *

UNITED STATES PATENT AND TRADEMARK OFFICE
CERTIFICATE OF CORRECTION

PATENT NO. : 6,576,896 B2
DATED : June 10, 2003
INVENTOR(S) : D. Figeys et al.

It is certified that error appears in the above-identified patent and that said Letters Patent is hereby corrected as shown below:

<u>Title page,</u>
Item [74], *Attorney, Agent or Firm*, "Christenson" should read -- Christensen --
Item [56], References Cited, OTHER PUBLICATIONS, *"Americal"* should read
-- *American* --

<u>Column 50,</u>
Line 14, "a protein and peptide" should read -- a protein and a peptide --

Signed and Sealed this

Eighteenth Day of May, 2004

JON W. DUDAS
*Acting Director of the United States Patent and Trademark Office*